United States Patent
Roy et al.

(10) Patent No.: US 6,904,912 B2
(45) Date of Patent: Jun. 14, 2005

(54) AUTOMATED INHALATION TOXICOLOGY EXPOSURE SYSTEM

(75) Inventors: Chad J. Roy, Myersville, MD (US); Justin M. Hartings, Clarksburg, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 130 days.

(21) Appl. No.: 09/919,741

(22) Filed: Jul. 31, 2001

(65) Prior Publication Data

US 2002/0103443 A1 Aug. 1, 2002

Related U.S. Application Data

(60) Provisional application No. 60/267,233, filed on Jan. 31, 2001.

(51) Int. Cl.[7] .............................................. A61M 11/00
(52) U.S. Cl. .................................. 128/203.18; 119/420
(58) Field of Search ...................... 128/203.14, 200.14; 119/420

(56) References Cited

U.S. PATENT DOCUMENTS

| | | |
|---|---|---|
| 3,548,840 A | 12/1970 | Baumqartner |
| 4,201,154 A | 5/1980 | Gowrie ........................ 119/15 |
| 4,216,741 A | 8/1980 | Moss ........................... 119/15 |

(Continued)

FOREIGN PATENT DOCUMENTS

| | | |
|---|---|---|
| EP | 0610171 B1 | 8/1994 |
| EP | 0 667 168 B1 | 6/2000 |
| WO | WO 91/06832 | 5/1991 |

*Primary Examiner*—Robert L. Nasser
(74) *Attorney, Agent, or Firm*—Elizabeth Arwine

(57) ABSTRACT

In one embodiment, a method includes but is not limited to exposing an animal to an inhalant; acquiring near real time measurement of at least respiration during said exposing; and calculating a received dose of the inhalant in response to the near real time measurement of the at least respiration during said exposing. In one embodiment, a method includes but is not limited to automatically controlling an environment of an inhalant chamber; and automatically controlling a concentration of an inhalant in the inhalant chamber. In one embodiment, a method includes but is not limited to displaying near real time measurement data related to an animal in an inhalant chamber. In addition to the foregoing, other method embodiments are described in the claims, drawings, and text forming a part of the present application. In one or more various embodiments, related systems include but are not limited to circuitry and/or programming for effecting the foregoing-described method embodiments; the circuitry and/or programming can be virtually any combination of hardware, software, and/or firmware configured to effect the foregoing-described method embodiments depending upon the design choices of the system designer. In one embodiment, a system includes but is not limited to at least one inhalant chamber; and at least one animal respiration sensor integral with the at least one inhalant chamber.

81 Claims, 18 Drawing Sheets

U.S. PATENT DOCUMENTS

| | | | |
|---|---|---|---|
| D262,320 S | 12/1981 | Monö | D24/62 |
| 4,305,347 A | 12/1981 | Hemenway et al. | 119/15 |
| 4,348,985 A | 9/1982 | Leong | 119/15 |
| 4,463,706 A | 8/1984 | Meister et al. | |
| 4,510,929 A | 4/1985 | Bordoni et al. | 128/200.14 |
| 4,520,808 A | 6/1985 | LaBauve | 128/200.14 |
| 4,532,892 A | 8/1985 | Kuzara | |
| 4,570,630 A | 2/1986 | Elliott et al. | 128/203.15 |
| 4,598,704 A | 7/1986 | Bordoni et al. | 128/200.14 |
| 4,674,490 A * | 6/1987 | Frankel et al. | 128/200.14 |
| 4,703,753 A | 11/1987 | Bordoni et al. | 128/200.14 |
| 4,721,060 A | 1/1988 | Cannon et al. | 119/15 |
| 4,787,384 A | 11/1988 | Campbell et al. | |
| 4,860,741 A | 8/1989 | Bernstein et al. | 128/204.18 |
| 4,940,051 A | 7/1990 | Lankinen | 128/200.18 |
| 5,099,792 A * | 3/1992 | Cannon et al. | 119/420 |
| 5,109,797 A | 5/1992 | Briant et al. | 119/15 |
| 5,156,776 A | 10/1992 | Loedding et al. | 261/27 |
| 5,186,164 A * | 2/1993 | Raghuprasad | 128/200.14 |
| 5,297,502 A | 3/1994 | Jaeger | 119/15 |
| 5,320,108 A * | 6/1994 | Cloutier | 600/529 |
| 5,379,777 A | 1/1995 | Lomask | 128/716 |
| 5,522,385 A * | 6/1996 | Lloyd et al. | 128/203.26 |
| 5,622,164 A | 4/1997 | Kilis et al. | 128/200.24 |
| 5,626,130 A | 5/1997 | Vincent et al. | 128/203.12 |
| 5,887,586 A | 3/1999 | Dahlback et al. | 128/204.22 |
| 5,896,829 A * | 4/1999 | Rothenberg et al. | 119/417 |
| 5,954,049 A * | 9/1999 | Foley et al. | 128/204.18 |
| 6,131,571 A | 10/2000 | Lampotang et al. | 128/204.21 |
| 6,138,668 A * | 10/2000 | Patton et al. | 128/200.14 |
| 6,263,872 B1 * | 7/2001 | Schuster et al. | 128/203.26 |
| 6,352,076 B1 * | 3/2002 | French | 119/420 |
| 6,725,859 B1 * | 4/2004 | Rothenberg et al. | 128/200.23 |

\* cited by examiner

```
                    ┌───────┐
                    │ start │──── 900
                    └───┬───┘
                        ▼
┌─────────────────────────────────────────────────────────────────────┐
│        automatically controlling an environment of an inhalant chamber │
│                            │                                         │
│                            ▼                                         │
│   ┌──────────────────────────────────────────────────────────────┐   │
│   │ dispersing either an organic or inorganic substance via electronic control of one or more │   │
│   │ inhalant dissemination devices (e.g., dispersing a substance having a form selected from an │   │
│   │ inhalant-form group including but not limited to a wet aerosol form, a dry aerosol form, a │   │
│   │ gaseous substance form, mist form, a fog form, a fume form, and an airborne substance │   │  ── 902
│   │                              form)                          │   │
│   └──────────────────────────────────────────────────────────────┘   │
│                            │                                         │
│                            ▼                                      1200│
└─────────────────────────────────────────────────────────────────────┘
                        │
                        ▼
┌─────────────────────────────────────────────────────────────────────┐
│  automatically controlling a concentration of an inhalant in the inhalant chamber │
│                                                                  ── 904│
└─────────────────────────────────────────────────────────────────────┘
                        │
                        ▼
                    ┌───────┐
                    │ stop  │──── 906
                    └───────┘
```

*Fig.12*

```
                    ┌─────────┐
                    │  start  │╱─ 900
                    └────┬────┘
                         │
                         ▼
┌─────────────────────────────────────────────────────────────────────┐
│        automatically controlling an environment of an inhalant chamber │
│                            │                                         │
│                            ▼                                         │
│  ┌───────────────────────────────────────────────────────────────┐   │
│  │ dispersing either an organic or inorganic substance via electronic control of one or more │   │
│  │ inhalant dissemination devices (e.g., controlling the one or more inhalant dissemination  │   │
│  │ devices via one or more Proportional Integral Derivative (PID) controllers respectively   │   │
│  │ receiving input from one or more dissemination-related sensors selected from the          │── 902
│  │ dissemination-related-sensor group including but not limited to a chamber pressure        │
│  │ monitor, an inhalant-concentration sensor, and a gas sensor)                              │
│  └───────────────────────────────────────────────────────────────┘   │
│                                                                      │
│                                                                1300  │
└──────────────────────────────┬───────────────────────────────────────┘
                               ▼
┌─────────────────────────────────────────────────────────────────────┐
│  automatically controlling a concentration of an inhalant in the inhalant chamber │── 904
└──────────────────────────────┬──────────────────────────────────────┘
                               │
                               ▼
                         ┌─────────┐
                         │  stop   │╱─ 906
                         └─────────┘
```

*Fig.13*

AUTOMATED INHALATION TOXICOLOGY EXPOSURE SYSTEM

CROSS-REFERENCE(S) TO RELATED APPLICATION(S)

This patent application hereby incorporates by reference in its entirety the pending U.S. Provisional Patent Application No. 60/267,233, filed Jan. 31, 2001, entitled AUTOMATED INHALATION TOXICOLOGY EXPOSURE SYSTEM, and naming Chad J. Roy and Justin M. Hartings as inventors; this patent application also claims the benefit of the foregoing-referenced Provisional Patent Application No. 60/267,233 under the auspices of 35 U.S.C. 119(e).

FIELD OF THE INVENTION

The present application relates, in general, to inhalant systems.

BACKGROUND OF THE INVENTION

Inhalation exposure studies are generally performed using inhalant systems. In an inhalation exposure study, an animal is usually exposed to an organic or inorganic inhalant within the confined space of an inhalant chamber forming part of an inhalant system.

In the related art, an inhalant system is typically one that provides mechanisms for exposing an animal to an inhalant. The inventors named herein ("inventors") have noticed several deficiencies and/or unmet needs associated with related-art inhalant systems, a few of which will now be set forth (other related-art deficiencies and/or unmet needs will become apparent in the detailed description below).

The inventors have discovered that related-art inhalant systems tend to provide poor reproducibility of scientific experiments. The inventors have noted that delivery of inhalants, environmental control, and monitoring in related-art inhalant systems is generally poorly controlled and/or monitored (e.g., by a human engaging in real-time manipulation of valves and motors and/or near real-time viewing and recordation of data presented on displays). Accordingly, insofar as human actions tend to be notoriously difficult to reproduce, the inventors have concluded that related-art inhalant systems tend to provide poor reproducibility. That is, precision and accuracy of inhalation experiments suffer because the users of related-art inhalant systems are neither able to exactly reproduce or actively record deviations of both intrinsic and extrinsic factors from experiment to experiment.

Insofar as inhalant systems are generally used to perform scientific experiments, it is desirable that the inhalant systems provide high reproducibility of scientific experiments so that experimental claims can be checked and validated. Unfortunately, related-art inhalant systems do not provide high reproducibility of scientific experiments. Accordingly, it is apparent that a need exists for inhalant systems that provide high reproducibility of scientific experiments, and that at present this need is going unmet in the related art.

In addition to the foregoing, the inventors have discovered that related-art inhalant systems do not incorporate near real-time measurement of respiratory function of test animals for purposes of dosimetry. That is, in general, related-art methods of inhalant dose calculation rely on physiologic trends based on historical data related to animals similar to those under test. Insofar as physiology varies from animal to animal, the inventors have recognized that it would be advantageous to have methods and systems, which provide, among other things, inhalant systems capable of determining inhalant dosage via near real-time acquisition of respiration of a test animal. Unfortunately, related-art inhalant systems are not, in general, capable of determining inhalant dosage via near real-time acquisition of respiration of a test animal. Accordingly, it is apparent that a need exists for inhalant systems capable of determining inhalant dosage via near real-time acquisition of respiration of a test animal.

SUMMARY OF THE INVENTION

The inventors have devised methods and systems, which provide, among other things, inhalant systems capable of achieving high reproducibility of scientific experiments. In addition, the inventors have devised methods and systems, which provide, among other things, inhalant systems capable of determining inhalant dosage via near real-time acquisition of respiration of a test animal.

In one embodiment, a method includes but is not limited to exposing an animal to an inhalant; acquiring near real time measurement of at least respiration during said exposing; and calculating a received dose of the inhalant in response to the near real time measurement of the at least respiration during said exposing.

In one embodiment, a method includes but is not limited to automatically controlling an environment of an inhalant chamber; and automatically controlling a concentration of an inhalant in the inhalant chamber.

In one embodiment, a method includes but is not limited to displaying near real time measurement data related to an animal in an inhalant chamber.

In addition to the foregoing, other method embodiments are described in the claims, drawings, and text forming a part of the present application.

In one or more various embodiments, related systems include but are not limited to circuitry and/or programming for effecting the foregoing-described method embodiments; the circuitry and/or programming can be virtually any combination of hardware, software, and/or firmware configured to effect the foregoing-described method embodiments depending upon the design choices of the system designer. In one embodiment, a system includes but is not limited to at least one inhalant chamber; and at least one animal respiration sensor integral with the at least one inhalant chamber.

The foregoing is a summary and thus contains, by necessity; simplifications, generalizations and omissions of detail; consequently, those skilled in the art will appreciate that the summary is illustrative only and is NOT intended to be in any way limiting. Other aspects, inventive features, and advantages of the devices and/or processes described herein, as defined solely by the claims, will become apparent in the non-limiting detailed description set forth herein.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 12 shows that in one implementation method step 902 can include method step 1200.

FIG. 13 depicts that in one implementation method step 902 can include method step 1300.

The use of the same reference symbols in different drawings indicates similar or identical items.

DETAILED DESCRIPTION OF THE
PREFERRED EMBODIMENT

Figure 1:
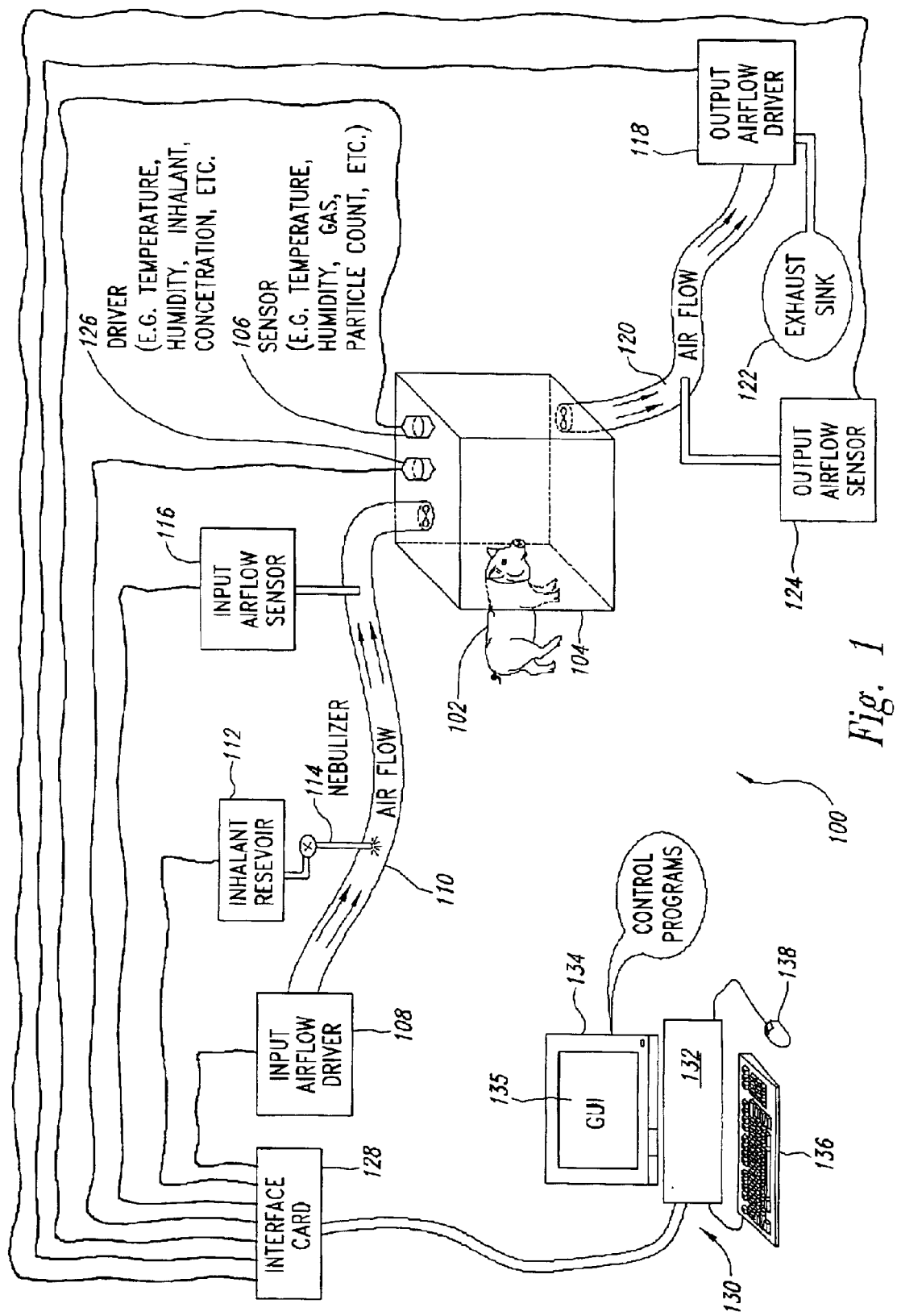
FIG. 1 shows a high level pictographic representation of inhalant exposure and monitoring system 100.

With reference now to FIG. 1, shown is a high level pictographic representation of inhalant exposure and monitoring system 1100. Depicted is inhalant toxicology exposure system 100. Illustrated is animal 102 contained within inhalant chamber 104. Shown integral with inhalant chamber 104 is sensor 106, which is intended to be indicative of one or more types of sensors integral with various parts of inhalant toxicology exposure system 100. For example, sensor 106 is meant to be indicative of a variety of different types of sensors, such as temperature sensors, humidity sensors, particle count sensors, gas concentration sensors, etcetera, and even though sensor 106 is shown integral with inhalant chamber 104, sensor 106 is meant to be indicative of sensors positioned throughout various parts of inhalant toxicology exposure system 100.

Further with respect to FIG. 1, depicted is input airflow driver 108 (e.g., an air pump) connected to drive air through input air hose 110 and into inhalant chamber 104. Illustrated is inhalant reservoir 112 (e.g., a reservoir for inhalants such as biological aerosols) that feeds nebulizer 114, and allows nebulizer 114 to deposit an inhalant into input air hose 110. Nebulizer 114 and inhalant reservoir 112 are meant to be collectively indicative of a variety of different types of organic or inorganic substance dispensing units, such as wet aerosol dispensing units, a dry aerosol dispensing units, a gaseous substance dispensing units, mist dispensing units, a fog dispensing units a fume dispensing units, and an airborne substance dispensing units, etc.), and even though nebulizer 114 is shown integral with input air hose 110, nebulizer 114 and inhalant reservoir 112 are meant to be collectively indicative of dispensing units positioned throughout various parts of inhalant toxicology exposure system 100. Further depicted is input airflow sensor 116, which detects input airflow volume, and even though input airflow sensor 116 is shown integral with input air hose 110, input airflow sensor 116 is meant to be indicative of input airflow sensors positioned throughout various parts of inhalant toxicology exposure system 100, where such various parts are in the air inflow path.

Further with respect to FIG. 1, depicted is output airflow driver 118 (e.g., a fan, or a vacuum pump) connected to drive air through output air hose 120 and into exhaust sink 122 (e.g., a chlorine bleach reservoir sufficient to kill/neutralize organic inhalants such as biological aerosols). Illustrated is output airflow sensor 124, which detects output airflow volume, airflow and even though output airflow sensor 124 is shown integral with output air hose 120, output airflow sensor 124 is meant to be indicative of output airflow sensors positioned throughout various parts of inhalant toxicology exposure system 100, where such various parts are in the air outflow path.

Further with respect to FIG. 1, shown integral with inhalant chamber 104 is driver 126, which is intended to be indicative of one or more types of drivers integral with various parts of inhalant toxicology exposure system 100. For example, driver 126 is meant to be indicative of a variety of different types of drivers, such as temperature drivers (e.g., heaters and/or coolers), humidity drivers (e.g., humidifiers and/or dehumidifiers), inhalant concentration drivers (e.g., the various types of organic and inorganic dispensing units described herein), etc. and even though driver 126 is shown integral with inhalant chamber 104, driver 126 is meant to be indicative of drivers positioned throughout various parts of inhalant toxicology exposure system 100.

Lastly with respect to FIG. 1, shown is that the various sensors and drivers of inhalant toxicology and exposure system are operably connected (e.g., via electrical connections capable of carrying digital and/or analog information) with interface card 128. Depicted is that interface card 128 is operably connected with data processing system 130 which includes system unit housing 132, video display device 134 (shown as displaying a graphical user interface (GUI) 135), keyboard 136, and mouse 138. In one implementation, one or more control programs 140 reside within and run on data processing system 130, where such one or more control programs control the various sensors and drivers shown in order to effect the processes described herein. Data processing system 130 may be implemented utilizing any suitable computer such as a DELL portable computer system, a product of Dell Computer Corporation, located in Round Rock, Tex.; Dell is a trademark of Dell Computer Corporation.

Following are a series of flowcharts depicting implementations of processes. For ease of understanding, the flowcharts are organized such that the initial flowcharts present implementations via an overall "big picture" viewpoint and thereafter the following flowcharts present alternate implementations and/or expansions of the "big picture" flowcharts as either substeps or additional steps building on one or more earlier-presented flowcharts. Those having ordinary skill in the art will appreciate that the style of presentation utilized herein (e.g., beginning with a presentation of a flowchart(s) presenting an overall view and thereafter providing additions to and/or further details in subsequent flowcharts) generally allows for a rapid and easy understanding of the various process implementations.

Figure 2:
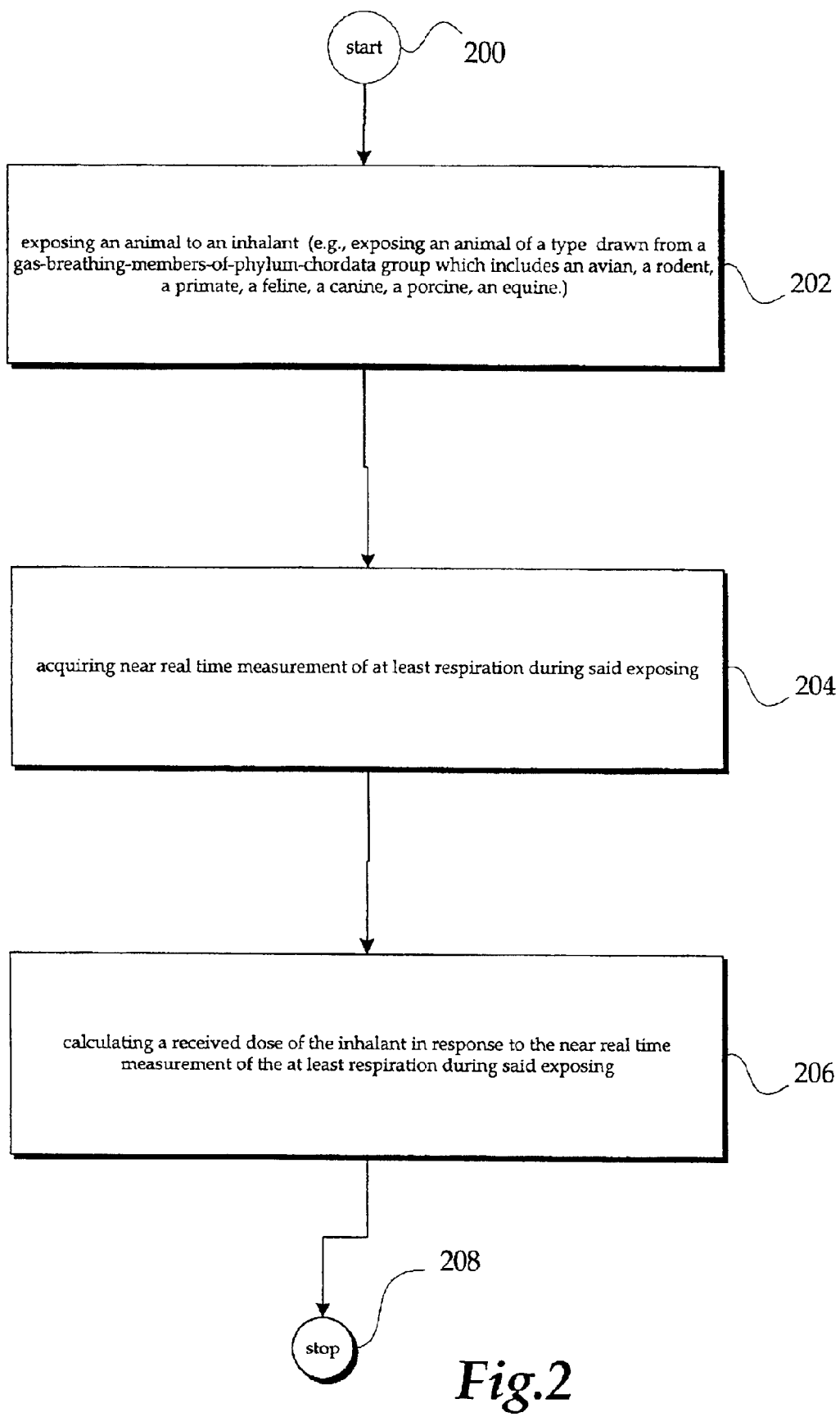
FIG. 2 shows the start of the process of exposing an animal to an inhalant.

With reference now to FIG. 2, shown is an implementation of a high-level logic flowchart depicting a process. Method step 200 shows the start of the process. Method step 202 depicts exposing an animal to an inhalant (e.g., exposing an animal of a type drawn from a gas-breathing-members-of-phylum-chordata group which includes an avian, a rodent, a primate, a feline, a canine, a porcine, an equine). In one device implementation, method step 202 is achieved by introducing an inhalant (e.g., an aerosolized form of a pathogen, such as anthrax or smallpox) from an inhalant reservoir (e.g., inhalant reservoir 112) into an inhalant chamber (e.g., inhalant chamber 104) containing all or part of an animal.

Method step 204 illustrates acquiring near real time measurement of at least respiration during said exposing. In one device implementation, method step 204 is achieved by via a respiration sensor (e.g., a pressure sensor implementation of sensor 106) integral with an inhalant chamber (e.g., inhalant chamber 104).

Method step 206 shows calculating a received dose of the inhalant in response to the near real time measurement of the at least respiration during said exposing. In one device implementation, method step 206 is achieved via a processor (e.g., a processor internal to data processing system 130) running software that calculates a dose of the inhalant received by the animal, where such calculation is based at least in part on the near real time measurement of respiration.

Method step 208 illustrates the end of the process.

For additional examples of the process of FIG. 2 and device implementations thereof, please see herein incorporated by reference Provisional Patent Application No. 60/267,233.

Figure 3:
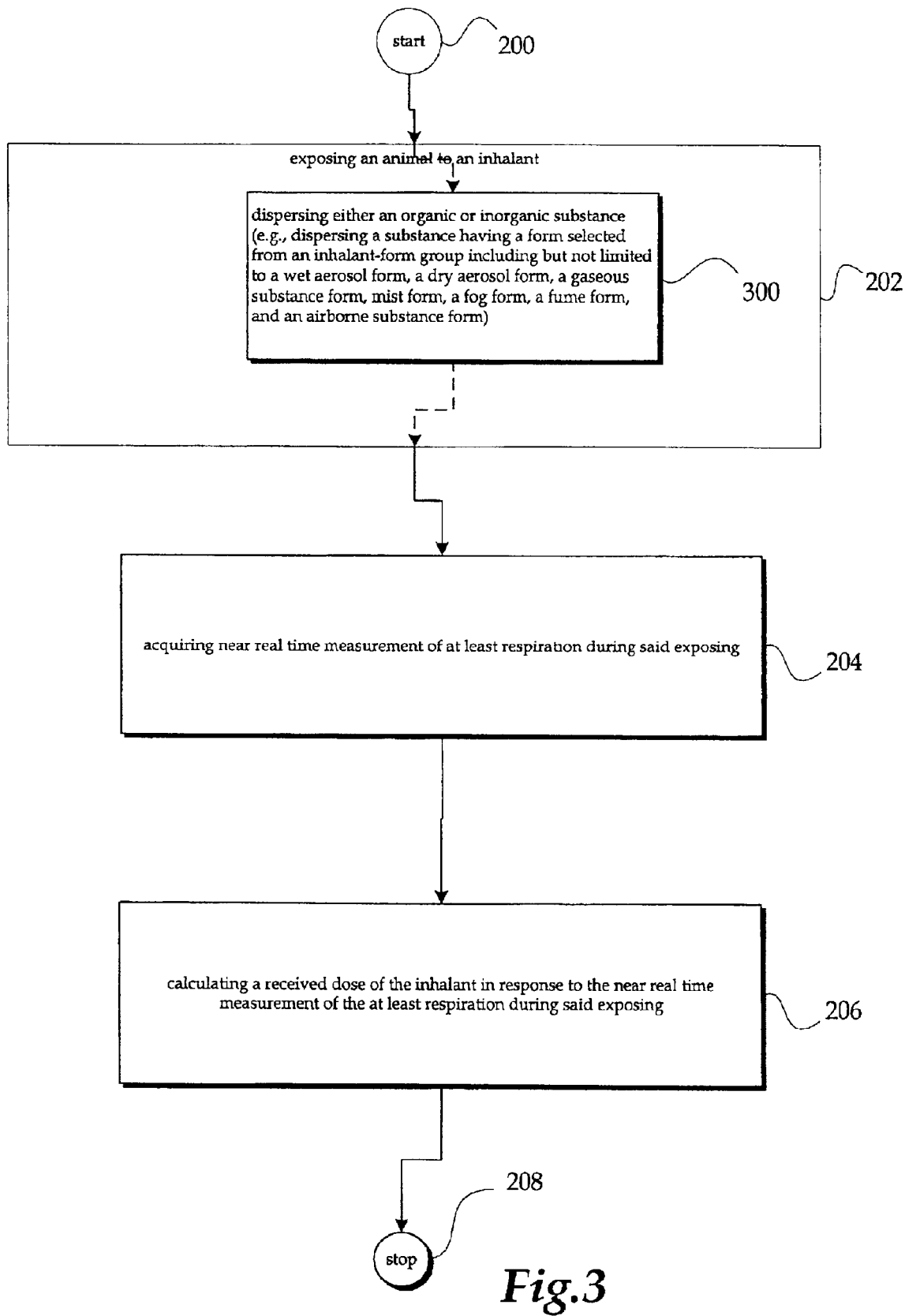
FIG. 3 shows that in one implementation method step 202 can include method step 300.

With reference now to FIG. 3, shown is an implementation of the high-level logic flowchart shown in FIG. 2. Depicted in FIG. 3 is that in one implementation method step 202 can include method step 300. Illustrated is that in one implementation exposing an animal to an inhalant can include, but is not limited to, dispersing either an organic or inorganic substance (e.g., dispersing a substance having a form selected from an inhalant-form group including but not limited to a wet aerosol form, a dry aerosol form, a gaseous substance form, mist form, a fog form, a fume form, and an airborne substance form). In one device implementation, method step 300 is achieved by activation of a nebulizer (e.g., nebulizer 114) that feeds an input airflow (e.g., input airflow flowing from input air hose 110 into inhalant chamber 104) into an inhalant chamber (e.g., inhalant chamber 104).

For additional examples of the process of FIG. 3 and device implementations thereof, please see herein incorporated by reference Provisional Patent Application No. 60/267,233. The remaining method steps of FIG. 3 function substantially as described elsewhere herein.

Figure 4:
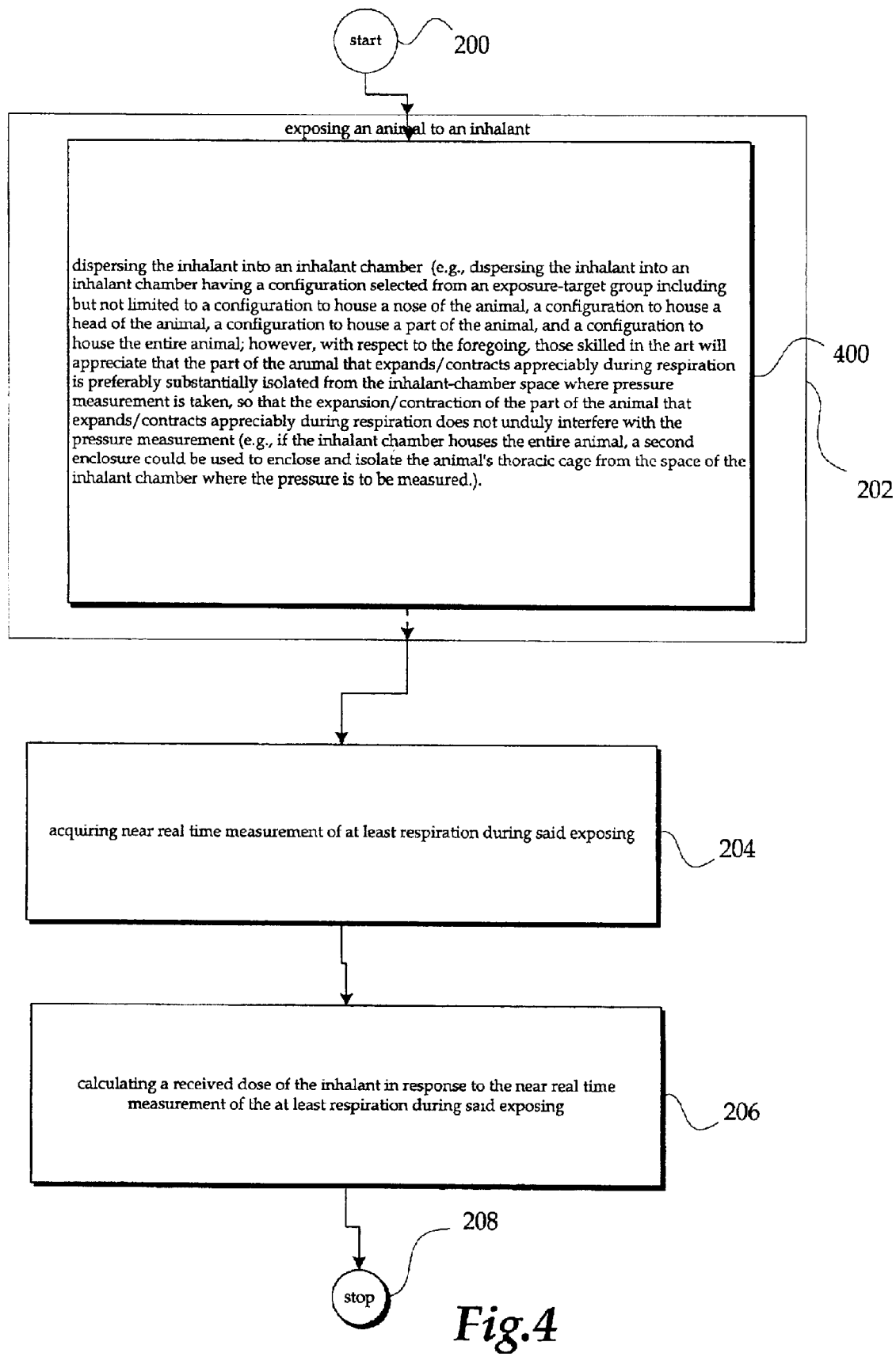
FIG. 4 depicts that in one implementation method step 202 can include method step 400.

With reference now to FIG. 4, shown is an implementation of the high-level logic flowchart shown in FIG. 2. Depicted in FIG. 4 is that in one implementation method step 202 can include method step 400. Illustrated is that in one implementation exposing an animal to an inhalant can include, but is not limited to, dispersing the inhalant into an inhalant chamber (e.g., dispersing the inhalant into an inhalant chamber having a configuration selected from an exposure-target group including but not limited to a configuration to house a nose of the animal, a configuration to house a head of the animal, a configuration to house a part of the animal, and a configuration to house the entire animal; however, with respect to the foregoing, those skilled in the art will appreciate that the part of the animal that expands/contracts appreciably during respiration is preferably substantially isolated from the inhalant-chamber space where pressure measurement is taken, so that the expansion/contraction of the part of the animal that expands/contracts appreciably during respiration does not unduly interfere with the pressure measurement (e.g., if the inhalant chamber houses the entire animal, a second enclosure could be used to enclose and isolate the animal's thoracic cage from the space of the inhalant chamber where the pressure is to be measured.). In one device implementation, method step 400 is achieved by activation of a nebulizer (e.g., nebulizer 114) which feeds an input airflow (e.g., input airflow flowing from input air hose 110 into inhalant chamber 104) into an inhalant chamber (e.g., inhalant chamber 104) constructed to enclose either the nose, head, part, or all of the animal in a fashion such that gaseous input and egress from the inhalant chamber are controlled.

For additional examples of the process of FIG. 4 and device implementations thereof, please see herein incorporated by reference Provisional Patent Application No. 60/267,233. The remaining method steps of FIG. 4 function substantially as described elsewhere herein.

Figure 5:
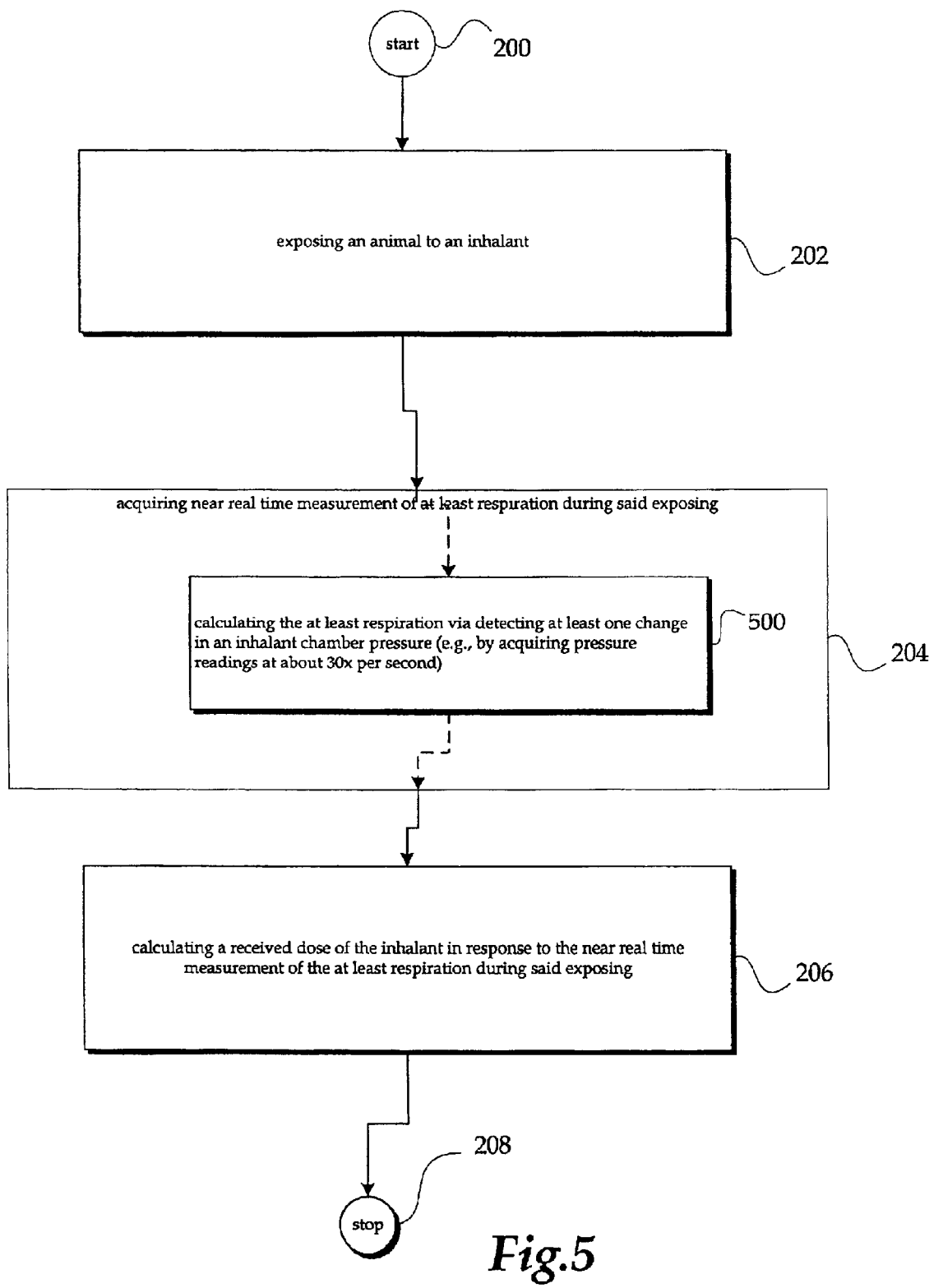
FIG. 5 shows that in one implementation method step 204 can include method step 500.

With reference now to FIG. 5, shown is an implementation of the high-level logic flowchart shown in FIG. 2. Depicted in FIG. 5 is that in one implementation method step 204 can include method step 500. Illustrated is that in one implementation acquiring near real time measurement of at least respiration during said exposing can include, but is not limited to, calculating the at least respiration via detecting at least one change in an inhalent chamber pressure (e.g., by acquiring pressure readings at about 30× per second). In one device implementation, method step 500 is achieved via a processor (e.g., a processor internal to data processing system 130) running software which calculates either or both inspiration and expiration by an animal in response to a pressure reading detected by a pressure transducer (e.g., a pressure sensor implementation of sensor 106) integral with an inhalation chamber (e.g., inhalation chamber 104). *

* Those skilled in the art will recongize that the change in the inhalent chamber pressure caused by the animal's repiratory function could also be measured indirectly by detecting a change in pressure in a second enclosure which isolates the animal's thoracic cage.

For additional examples of the process of FIG. 5 and device implementations thereof, please see herein incorporated by reference Provisional Patent Application No. 60/267,233. The remaining method steps of FIG. 5 function substantially as described elsewhere herein.

Figure 6:
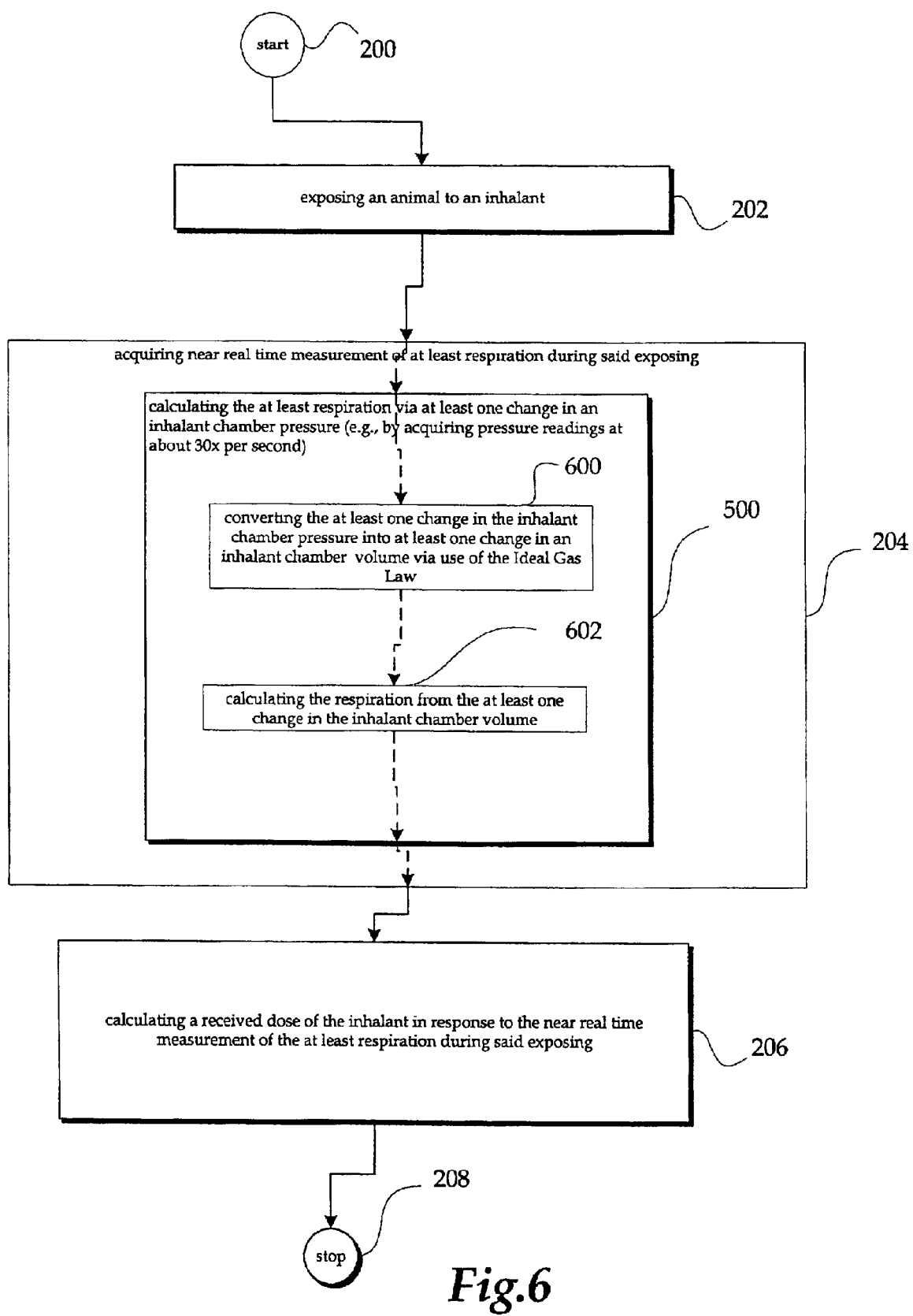
FIG. 6 depicts that in one implementation method step 500 can include method steps 600 and 602.

With reference now to FIG. 6, shown is an implementation of the high-level logic flowchart shown in FIG. 5. Depicted in FIG. 6 is that in one implementation method step 500 can include method steps 600 and 602. Illustrated is that in one implementation calculating the at least respiration via detecting at least one change in a chamber pressure can include, but is not limited to, converting the at least one change in the inhalant chamber pressure into at least one change in an inhalant chamber volume via use of the Ideal Gas Law. In one device implementation, method step 600 is achieved via a processor (e.g., a processor internal to data processing system 130) running software, which calculates either or both inspiration and expiration by an animal in response to a pressure reading detected by a pressure transducer (a pressure sensor implementation of sensor 106) integral with an inhalation chamber (e.g., inhalation chamber 104), via use of the Ideal Gas Law (e.g., PV=nRT, where p is the pressure, V is the volume, n is the number of moles, R is the gas constant, and T is the temperature.). Further illustrated is that in one implementation calculating the at least respiration via detecting at least one change in a chamber pressure can include, but is not limited to, calculating the respiration from the at least one change in the inhalant chamber volume. In one device implementation, method step 602 is achieved via a processor (e.g., a processor internal to data processing system 130) running software, which calculates either or both inspiration and expiration by an animal in response to the calculated change in volume such as was described in relation to method step 600.

For additional examples of the process of FIG. 6 and device implementations thereof, please see herein incorporated by reference Provisional Patent Application No. 60/267,233. The remaining method steps of FIG. 6 function substantially as described elsewhere herein.

Figure 7:
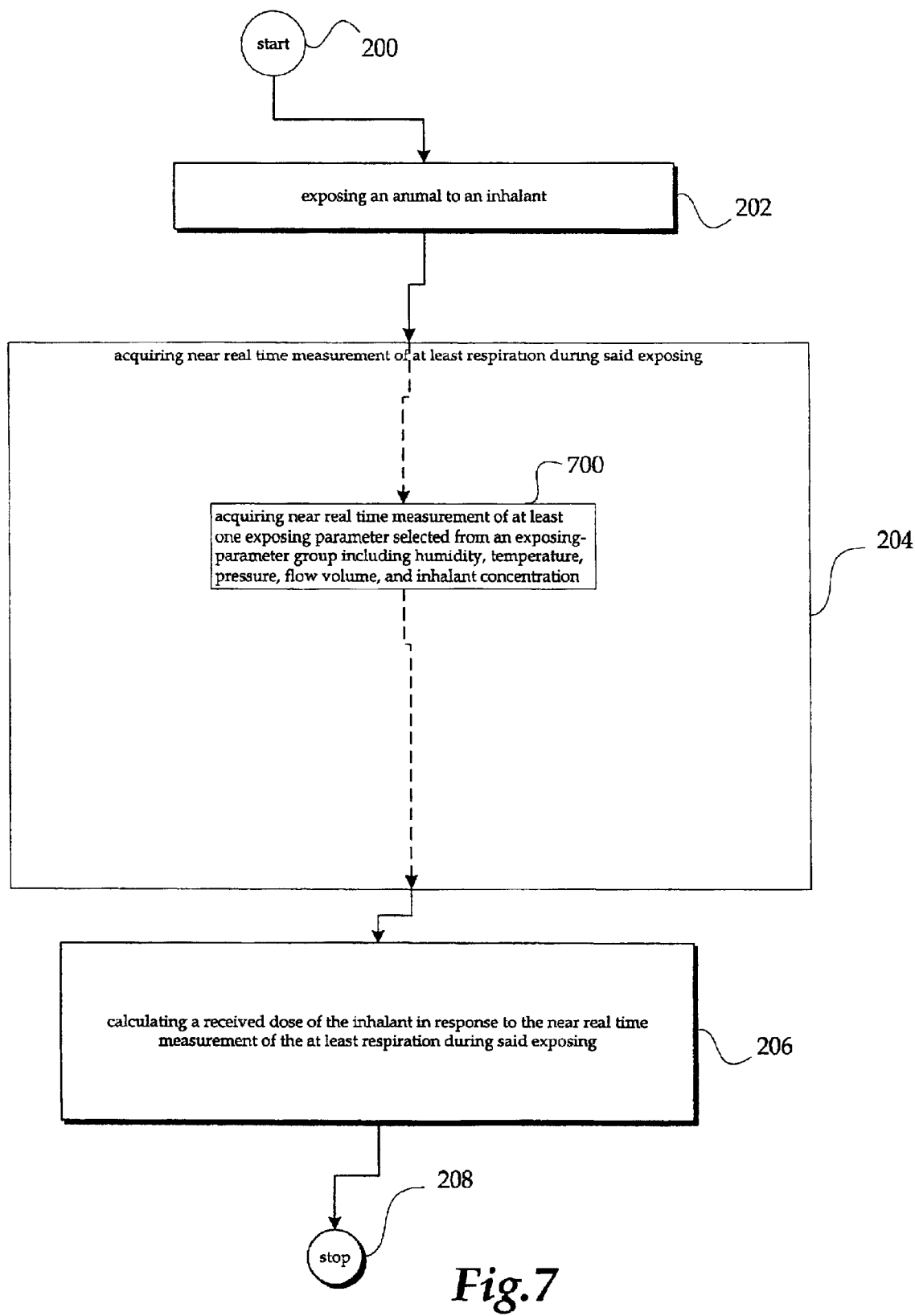
FIG. 7 shows that in one implementation method step 204 can include method step 700.

With reference now to FIG. 7, shown is an implementation of the high-level logic flowchart shown in FIG. 2. Depicted in FIG. 7 is that in one implementation method step 204 can include method step 700. Illustrated is that in one implementation acquiring near real time measurement of at least respiration during said exposing can include, but is not limited to, acquiring near real time measurement of at least one exposing parameter selected from an exposing-parameter group including humidity, temperature, pressure, flow volume, and inhalant concentration. In one device implementation, method step 700 is achieved via a processor (e.g., a processor internal to data processing system 130) running software, which monitors and collects data from humidity, pressure, flow volume, and/or inhalant concentration sensors (e.g., humidity sensor, pressure sensor, flow volume sensor, and inhalant concentration sensor, etc. implementations of sensor 106) integral with an inhalation chamber (e.g., inhalation chamber 106).

For additional examples of the process of FIG. 7 and device implementations thereof, please see herein incorporated by reference Provisional Patent Application No. 60/267,233. The remaining method steps of FIG. 7 function substantially as described elsewhere herein.

Figure 8:
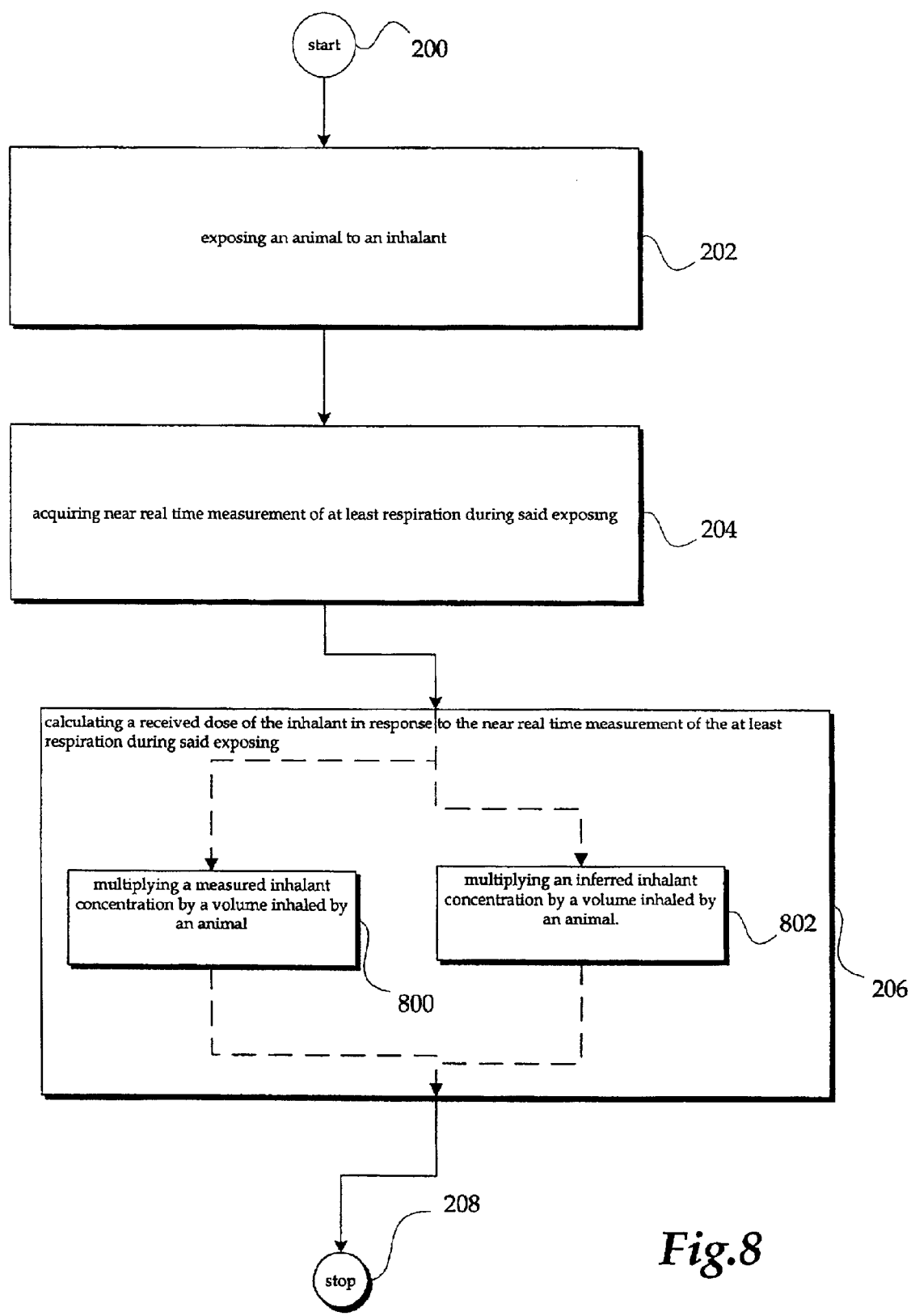
FIG. 8 shows that in one implementation method step 206 can include method step 800, while in another implementation method step 206 can include method step 802.

With reference now to FIG. 8, shown are alternate implementations of the high-level logic flowchart shown in FIG. 2. Depicted in FIG. 8 is that in one implementation method step 206 can include method step 800, while in another implementation method step 206 can include method step 802. Illustrated in method step 800 is that in one implementation calculating a received dose of the inhalant in response to the near real time measurement of the at least respiration during said exposing can include, but is not limited to, multiplying a measured inhalant concentration by a volume inhaled by an animal. In one device implementation, method step 800 is achieved via a processor (e.g., a processor internal to data processing system 130) running software which uses measured data in conjunction with a calculated volume of air inhaled by an animal in an inhalant chamber 104). Depicted in method step 802 is that in another implementation calculating a received dose of the inhalant in response to the near real time measurement of the at least respiration during said exposing can include, but is not limited to, multiplying an inferred inhalant concentration by a volume inhaled by an animal. In one device implementation, method step 800 is achieved via a processor (e.g., a processor internal to data processing system 130) running software which uses inferred data (e.g.. data inferred from directions to a nebulizer to dispense a certain aerosol concentration) in conjunction with a calculated volume of air inhaled by an animal in an inhalant chamber 104).

For additional examples of the process of FIG. 8 and device implementations thereof, please see herein incorporated by reference Provisional Patent Application No. 60/267,233. The remaining method steps of FIG. 8 function substantially as described elsewhere herein.

Figure 9:
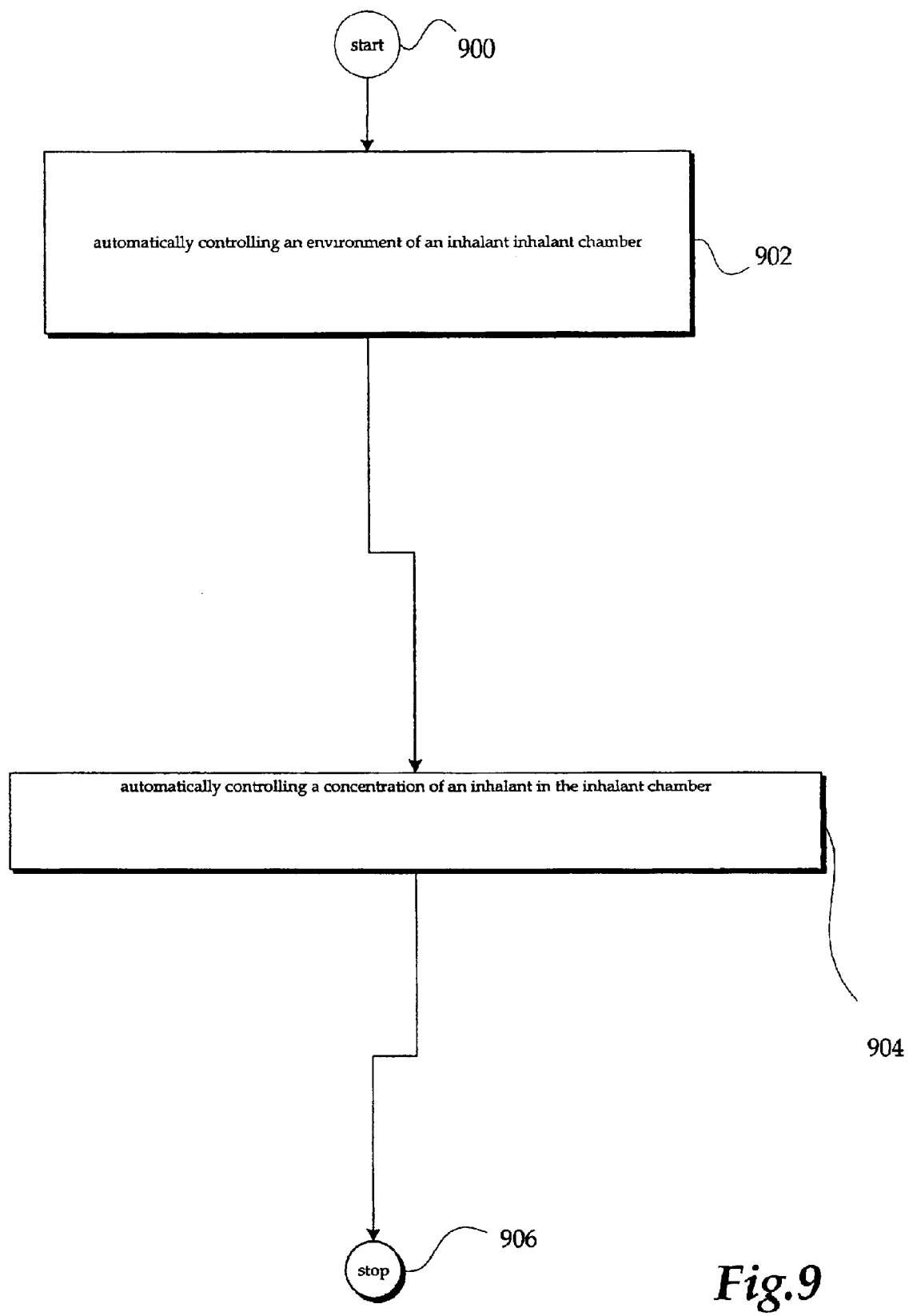
FIG. 9 shows a process that depicts automatically controls an environment of an inhalant chamber.

With reference now to FIG. 9, shown is an implementation of a high-level logic flowchart depicting a process. Method step 900 shows the start of the process. Method step 902 depicts automatically controlling an environment of an inhalant chamber. Method step 904 illustrates automatically controlling a concentration of an inhalant in the inhalant chamber. Method step 906 shows the end of the process.

For examples of the process of FIG. 9, please see the discussion here. For additional examples of the process of FIG. 9 and device implementations thereof, please see herein incorporated by reference Provisional Patent Application No. 60/267,233.

Figure 10:
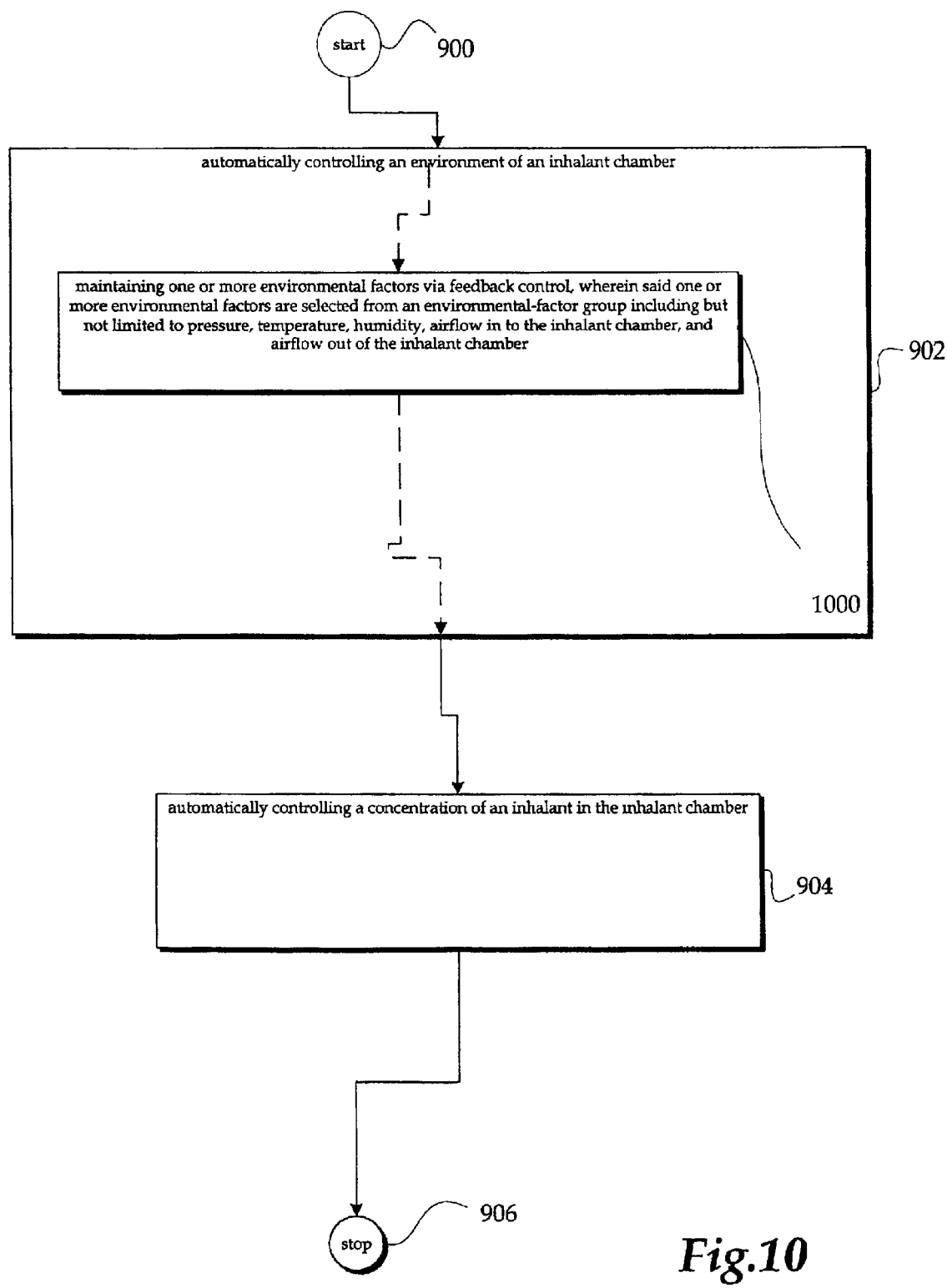
FIG. 10 shows that in one implementation method step 902 can include method step 1000.

With reference now to FIG. 10, shown is an implementation of the high-level logic flowchart shown in FIG. 9. Depicted in FIG. 10 is that in one implementation method step 902 can include method step 1000. Illustrated is that in one implementation automatically controlling an environment of an inhalant chamber can include, but is not limited to, maintaining one or more environmental factors via feedback control, wherein said one or more environmental factors are selected from an environmental-factor group including but not limited to pressure, temperature, humidity, airflow in to the inhalant chamber, and airflow out of the inhalant chamber. In one device implementation, method step 1000 is achieved via control software running on a processor (e.g., a processor internal to data processing system 130), where the control software maintains the one or more environmental factors at levels specified via user input to a graphical user interface.

For additional examples of the process of FIG. 10 and device implementations thereof, please see herein incorporated by reference Provisional Patent Application No. 60/267,233. The remaining method steps of FIG. 10 function substantially as described elsewhere herein.

Figure 11:
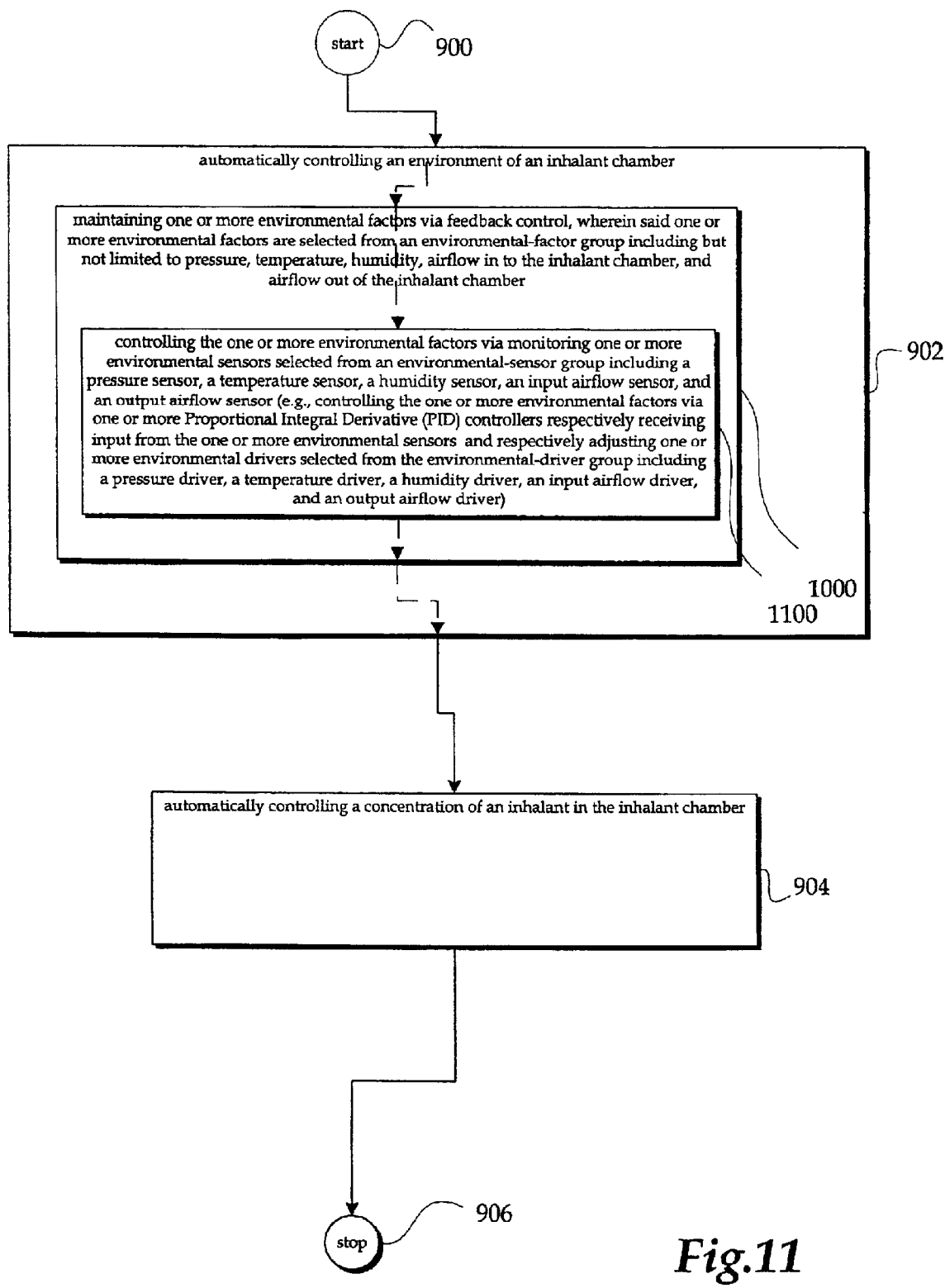
FIG. 11 depicts that in one implementation method step 1000 can include method step 1100.

With reference now to FIG. 11, shown is an implementation of the high-level logic flowchart shown in FIG. 10. Depicted in FIG. 11 is that in one implementation method step 1000 can include method step 1100. Illustrated is that in one implementation maintaining one or more environmental factors via feedback control, wherein said one or more environmental factors are selected from an environmental-factor group including but not limited to pressure, temperature, humidity, airflow in to the inhalant chamber, and airflow out of the inhalant chamber can include, but is not limited to, controlling the one or more environmental factors via monitoring one or more environmental sensors selected from an environmental-sensor group including a pressure sensor, a temperature sensor, a humidity sensor, an input airflow sensor, and an output airflow sensor (e.g., controlling the one or more environmental factors via one or more Proportional Integral Derivative (PID) controllers respectively receiving input from the one or more environmental sensors and respectively adjusting one or more environmental drivers selected from the environmental-driver group including a pressure driver, a temperature driver, a humidity driver, an input airflow driver, and an output airflow driver).

In one device implementation, method step 1100 is achieved via control software running on a processor (e.g., a processor internal to data processing system 130), where the control software collects data from one or more environmental sensors and uses one or more PID algorithms to adjust one or more devices which drive the one or more environmental factors.

For additional examples of the process of FIG. 11 and device implementations thereof, please see herein incorporated by reference Provisional Patent Application No. 60/267,233. The remaining method steps of FIG. 11 function substantially as described elsewhere herein.

With reference now to FIG. 12, shown is an implementation of the high-level logic flowchart shown in FIG. 9. Depicted in FIG. 12 is that in one implementation method step 902 can include method step 1200. Illustrated is that in one implementation automatically controlling an environment of an inhalant chamber can include, but is not limited to, dispersing either an organic or inorganic substance via electronic control of one or more inhalant dissemination devices (e.g., dispersing a substance having a form selected from an inhalant-form group including but not limited to a wet aerosol form, a dry aerosol form, a gaseous substance form, mist form, a fog form, a fume form, and an airborne substance form). In one device implementation, method step 1200 is achieved by activation of a nebulizer (e.g., nebulizer 114) that feeds an input airflow (e.g., input airflow flowing from input air hose 110 into inhalant chamber 10) into an inhalant chamber (e.g., inhalant chamber 104).

For additional examples of the process of FIG. 12 and device implementations thereof, please see herein incorporated by reference Provisional Patent Application No. 60/267,233. The remaining method steps of FIG. 12 function substantially as described elsewhere herein.

With reference now to FIG. 13, shown is an implementation of the high-level logic flowchart shown in FIG. 9. Depicted in FIG. 13 is that in one implementation method step 902 can include method step 1300. Illustrated is that in one implementation automatically controlling an environment of an inhalant chamber can include, but is not limited to, dispersing either an organic or inorganic substance via electronic control of one or more inhalant dissemination devices (e.g., controlling the one or more inhalant dissemination devices via one or more Proportional Integral Derivative (PID) controllers respectively receiving input from one or more dissemination-related sensors selected from the dissemination-related-sensor group including but not limited to a chamber pressure monitor, an inhalant-concentration sensor, and a gas sensor). In one device implementation, method step 1300 is achieved via control software running on a processor (e.g., a processor internal to data processing system 130), where the control software collects data from one or more dissemination-related sensors (e.g., various and sundry implementations of sensor(s) 106) and uses one or more PID algorithms to adjust one or more one or more inhalant dissemination devices (e.g., one or more implementations of the drivers and/or dissemination devices described herein).

For additional examples of the process of FIG. 13 and device implementations thereof, please see herein incorporated by reference Provisional Patent Application No. 60/267,233. The remaining method steps of FIG. 13 function substantially as described elsewhere herein.

Figure 14:
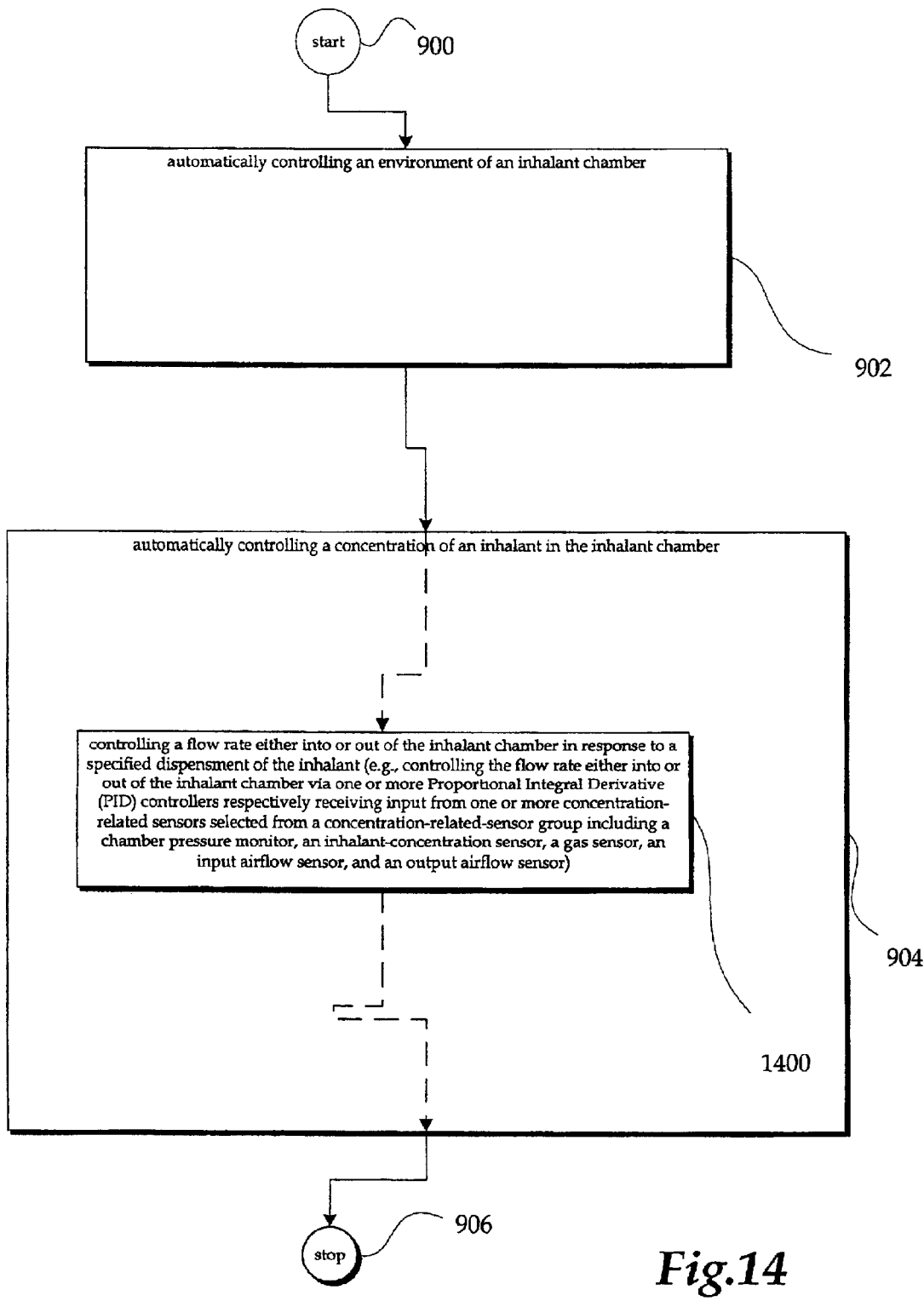
FIG. 14 depicts that in one implementation method step 902 can include method step 1400.

With reference now to FIG. 14, shown is an implementation of the high-level logic flowchart shown in FIG. 9. Depicted in FIG. 14 is that in one implementation method step 904 can include method step 1400. Illustrated is that in one implementation automatically controlling a concentration of an inhalant in the inhalant chamber, but is not limited to, controlling a flow rate either into or out of the inhalant chamber in response to a specified discernment of the inhalant (e.g., controlling the flow rate either into or out of the inhalant chamber via one or more Proportional Integral Derivative (PID) controllers respectively receiving input from one or more concentration-related sensors selected from a concentration-related-sensor group including a chamber pressure monitor, an inhalant-concentration sensor, a gas sensor, an input airflow sensor, and an output airflow sensor). In one device implementation, method step 1400 is achieved via control software running on a processor (e.g., a processor internal to data processing system 130), where the control software collects data from one or more concentration-related sensors (e.g., various and sundry concentration-related implementations of sensor(s) 106) and uses one or more PID algorithms to adjust one or more flow rate control devices (one or more implementations of the drivers and/or dissemination devices described herein).

For additional examples of the process of FIG. 14 and device implementations thereof, please see herein incorporated by reference Provisional Patent Application No. 60/267,233. The remaining method steps of FIG. 14 function substantially as described elsewhere herein.

Figure 15:
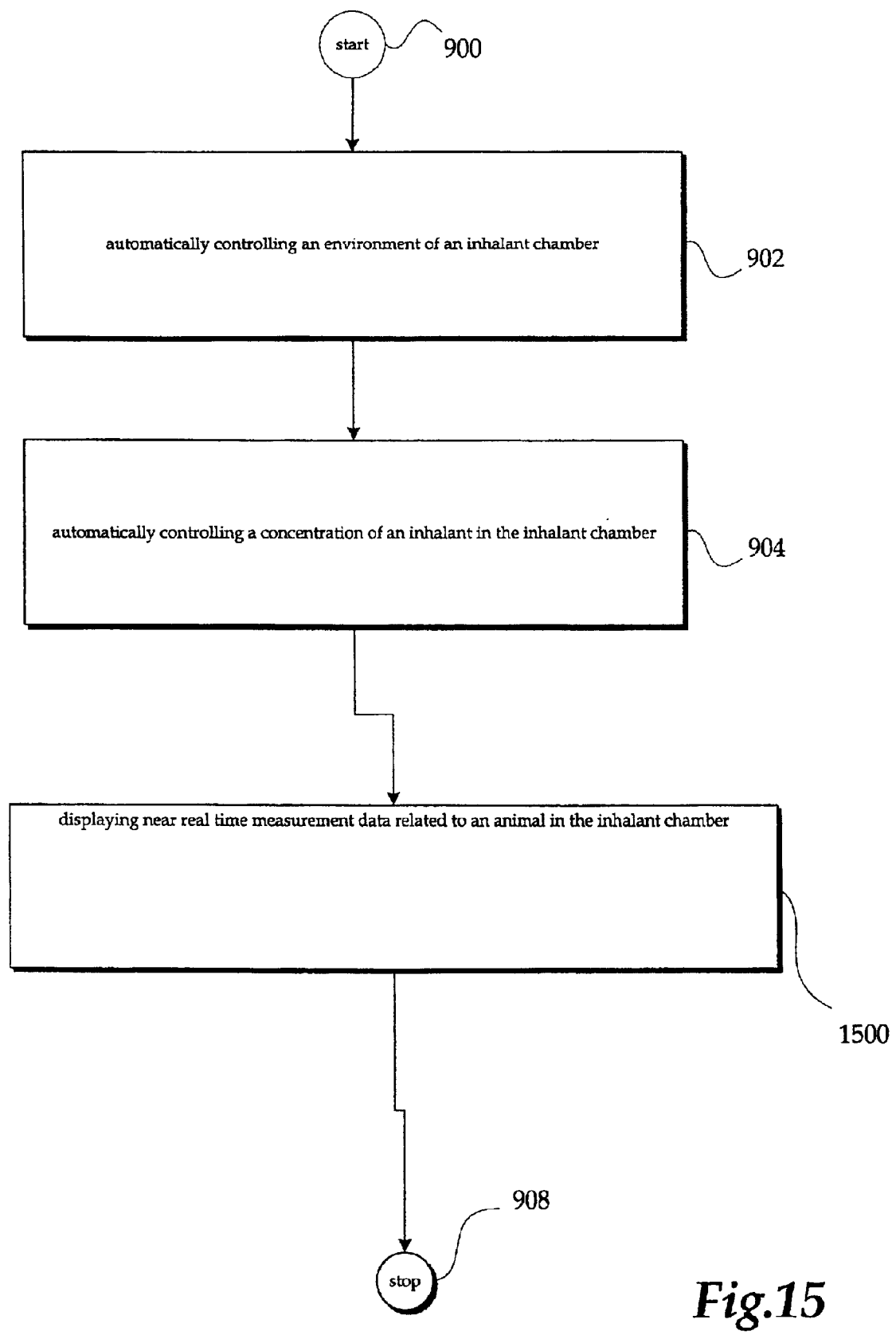
FIG. 15 shows that in one alternate implementation the process includes additional method step 1500.

With reference now to FIG. 15, shown is an alternate implementation of the high-level logic flowchart of FIG. 9. Shown is that in one alternate implementation the process includes additional method step 1500. Method step 1500 depicts displaying near real time measurement data related to an animal in the inhalant chamber. In one device implementation, method step 1500 is achieved via display of the near real time measurement data via a Graphical User Interface (e.g., GUI 135) displayed on a screen (e.g., display device 134) of a computer (e.g., data processing system 130).

For additional examples of the process of FIG. 15 and device implementations thereof, please see herein incorporated by reference Provisional Patent Application No. 60/267,233. The remaining method steps of FIG. 15 function substantially as described elsewhere herein.

Figure 16:
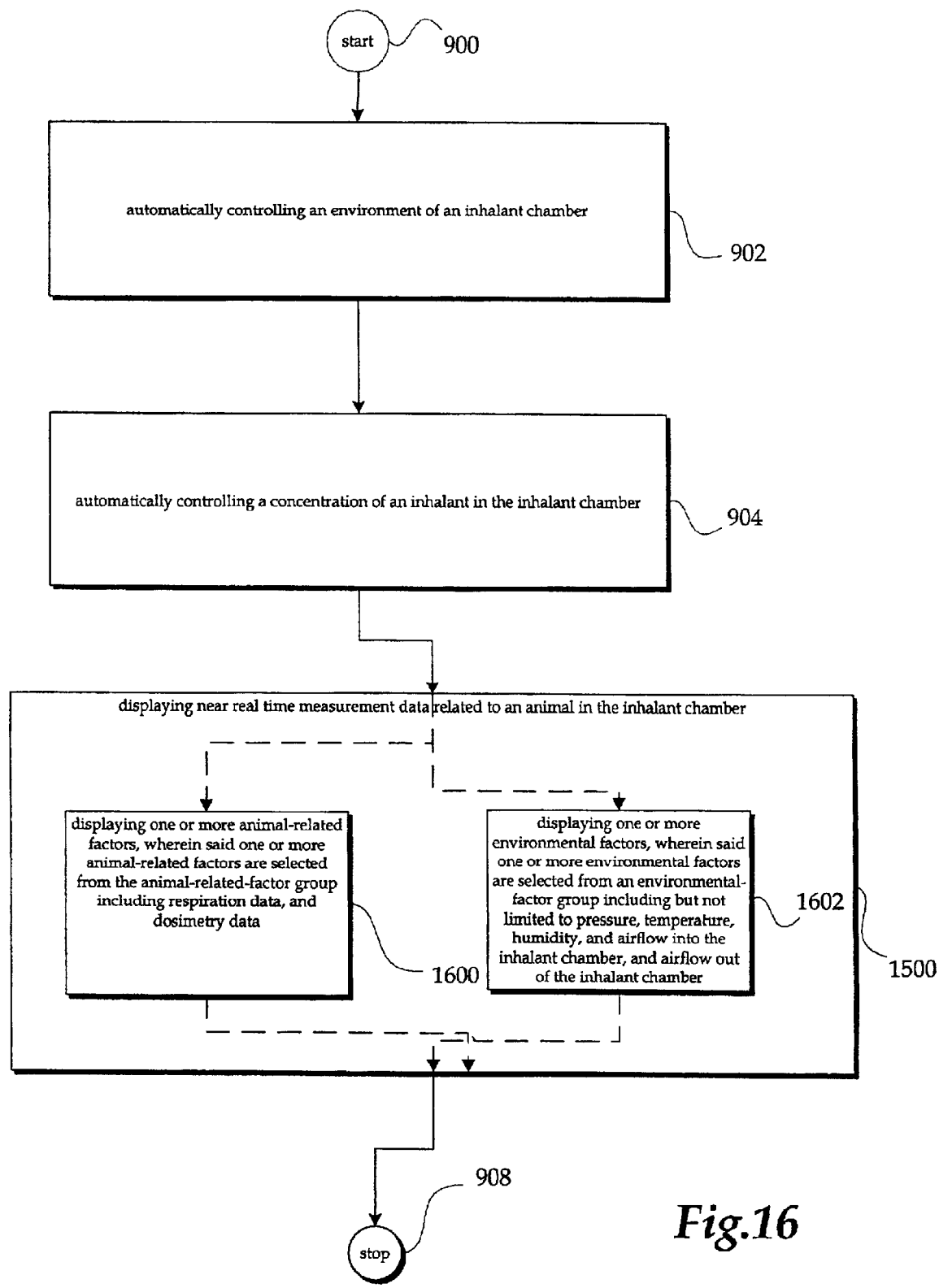
FIG. 16 shows that in one implementation method step 1500 can include method step 1600, while in another implementation method step 1500 can include method step 1602.

With reference now to FIG. 16, shown are alternate implementations of the high-level logic flowchart shown in FIG. 15. Depicted in FIG. 16 is that in one implementation method step 1500 can include method step 1600, while in another implementation method step 1500 can include method step 1602. Illustrated in method step 1600 is that in one implementation displaying near real time measurement data related to an animal in the inhalant chamber can include, but is not limited to, displaying one or more animal-related factors, wherein said one or more animal-related factors are selected from the animal-related-factor group including respiration data and dosimetry data. In one device implementation, method step 1600 is achieved via display of the one or more animal-related factors a Graphical User Interface (e.g., GUI 135) displayed on a screen (e.g., display device 134) of a computer (e.g., data processing system 130).

Further depicted in method step 1602 is that in another implementation displaying near real time measurement data related to an animal in the inhalant chamber can include, but is not limited to, displaying one or more environmental factors, wherein said one or more environmental factors are selected from an environmental-factor group including but not limited to pressure, temperature, humidity, and airflow into the inhalant chamber, and airflow out of the inhalant chamber. In one device implementation, method step 1602 is achieved via display of the one or more environmental factors a Graphical User Interface (e.g., GUI 135) displayed on a screen (e.g., display device 134) of a computer (e.g., data processing system 130).

For additional examples of the process of FIG. 16 and device implementations thereof, please see herein incorporated by reference Provisional Patent Application No. 60/267,233. The remaining method steps of FIG. 16 function substantially as described elsewhere herein.

Figure 17:
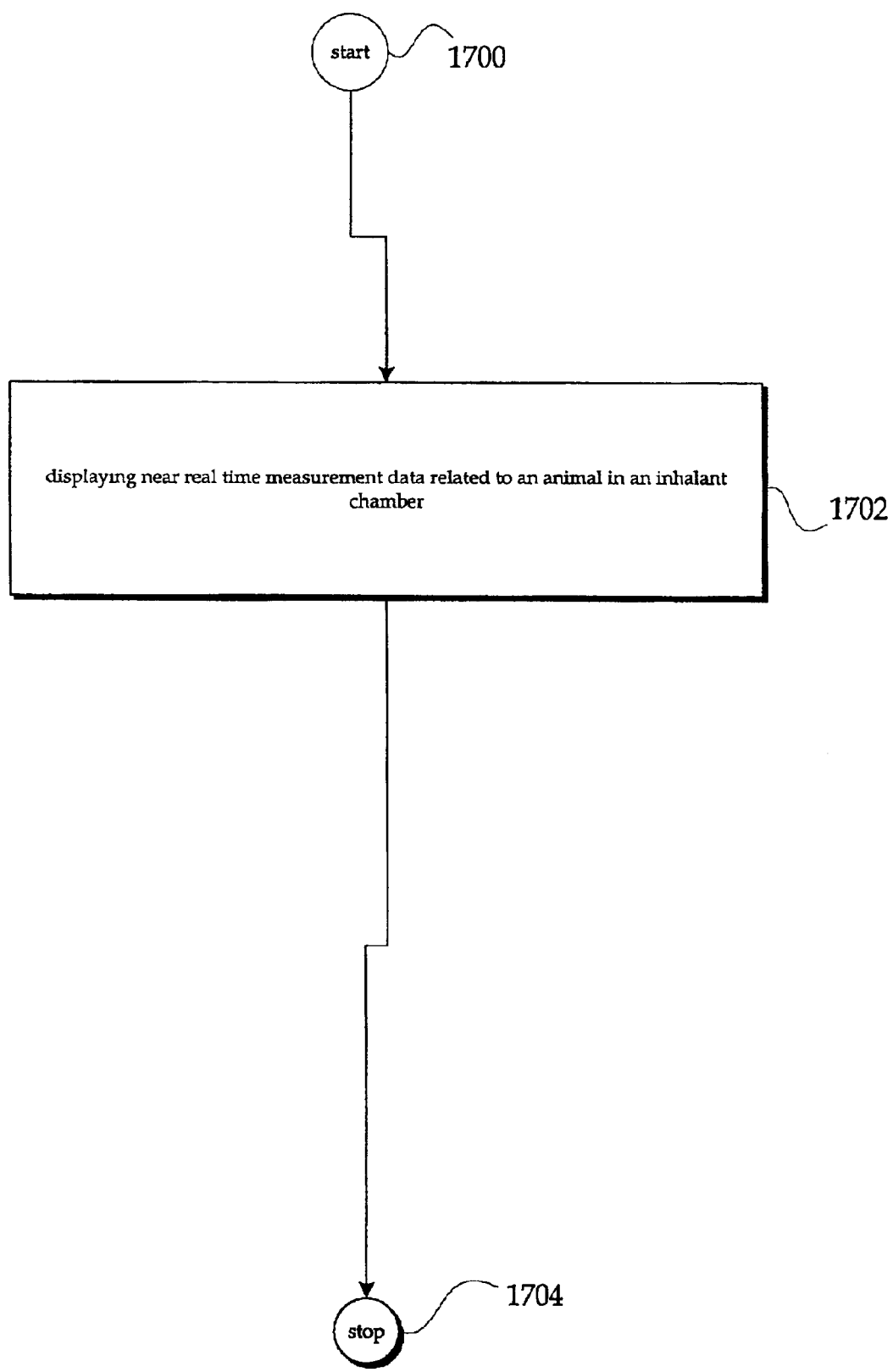
FIG. 17 depicts a process that displays near real time measurement data related to an animal in the inhalant chamber.

With reference now to FIG. 17, shown is a high-level logic flowchart depicting a process. Method step 1700 depicts the start of the process. Method step 1702 illustrates displaying near real time measurement data related to an animal in the inhalant chamber. In one device implementation, method step 1700 is achieved via display of the near real time measurement data a Graphical User Interface (e.g., GUI 135) displayed on a screen (e.g., display device 134) of a computer (e.g., data processing system 130). Method step 1704 shows the end of the process.

For additional examples of the process of FIG. 17 and device implementations thereof, please see herein incorporated by reference Provisional Patent Application No. 60/267,233.

Figure 18:
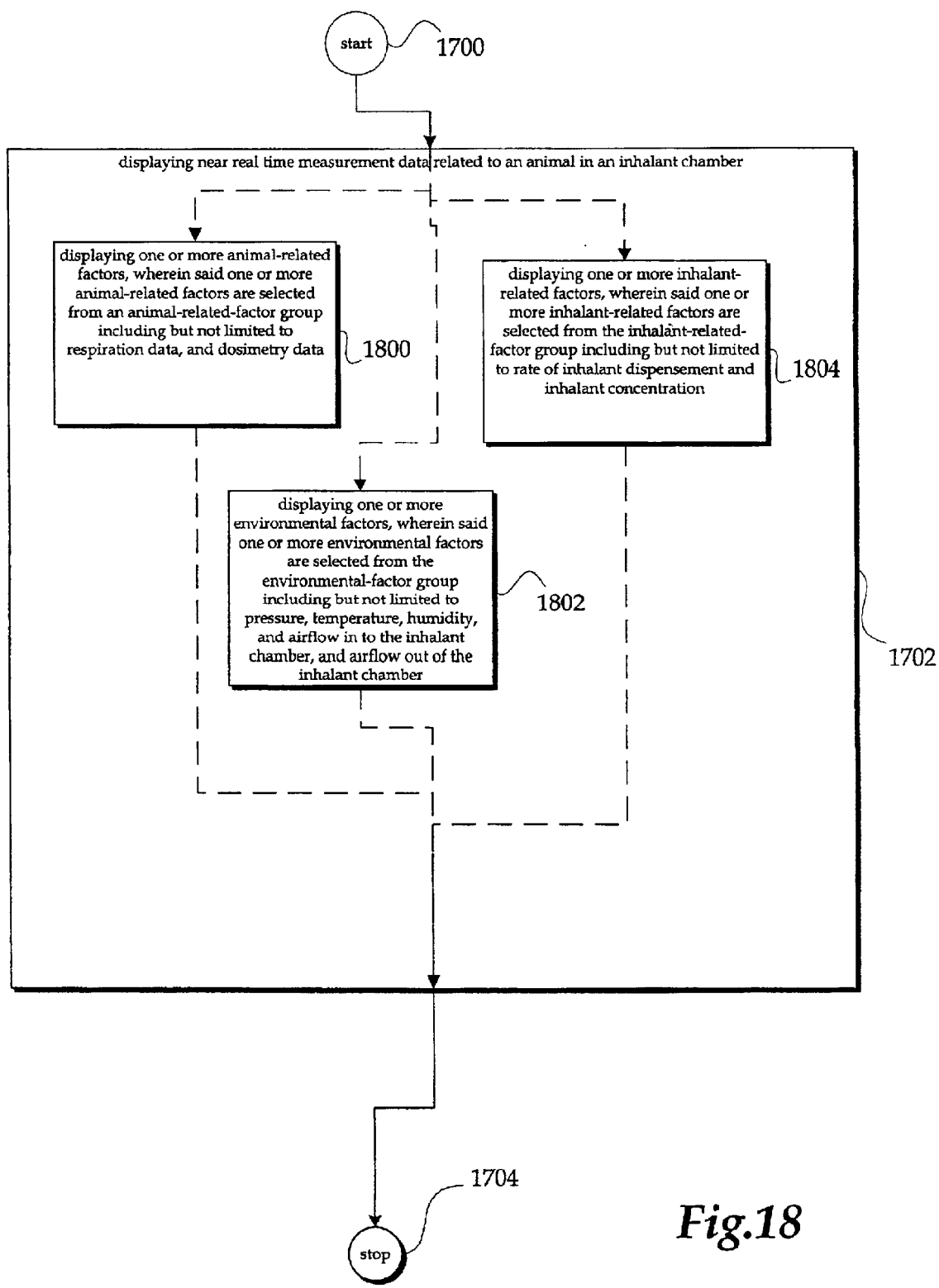
FIG. 18 shows that in one implementation method step 1702 can include method step 1800, while in another implementation method step 1702 can include method step 1802, while in yet another implementation method step 1702 can include method step 1804.

With reference now to FIG. 18, shown are alternate implementations of the high-level logic flowchart shown in FIG. 17. Depicted in FIG. 18 is that in one implementation method step 1702 can include method step 1800, while in another implementation method step 1702 can include method step 1802, while in yet another implementation method step 1702 can include method step 1804. Illustrated in method step 1800 is that in one implementation displaying near real time measurement data related to an animal in the inhalant chamber can include, but is not limited to, displaying one or more animal-related factors, wherein said one or more animal-related factors are selected from the animal-related-factor group including respiration data and dosimetry data. In one device implementation, method step 1600 is achieved via display of the one or more animal-related factors a Graphical User Interface (e.g., GUI 135) displayed on a screen (e.g., display device 134) of a computer (e.g., data processing system 130).

Further depicted in method step 1804 is that in another implementation displaying near real time measurement data related to an animal in the inhalant chamber can include, but is not limited to, displaying one or more environmental factors, wherein said one or more environmental factors are selected from an environmental-factor group including but not limited to pressure, temperature, humidity, and airflow into the inhalant chamber, and airflow out of the inhalant chamber. In one device implementation, method step 1802 is achieved via display of the one or more environmental factors a Graphical User Interface (e.g., GUI 135) displayed on a screen (e.g., display device 134) of a computer (e.g., data processing system 130).

Yet further depicted in method step 1804 is that in another implementation displaying near real time measurement data related to an animal in the inhalant chamber can include, but is not limited to, displaying one or more inhalant-related factors, wherein said one or more inhalant-related factors are selected from the inhalant-related-factor group including but not limited to rate of inhalant discernment and inhalant concentration. In one device implementation, method step 1804 is achieved via display of the one or more environmental factors a Graphical User Interface (e.g., GUI 135) displayed on a screen (e.g., display device 134) of a computer (e.g., data processing system 130).

For additional examples of the process of FIG. 18 and device implementations thereof, please see herein incorporated by reference Provisional Patent Application No. 60/267,233. The remaining method steps of FIG. 18 function substantially as described elsewhere herein.

Those having ordinary skill in the art will appreciate that in the discussion herein the same factors and/or sensors have sometimes appeared in different categories of sensors (e.g., the same sensors categorized as environmental sensors or inhalant-concentration sensors). Those skilled in the art will appreciate that this is because in some instances the factors and/or sensors have been designated as environmental (e.g., hold humidity constant at 66%) which usually (but not always) mitigates the ability to use such factors and/or sensors to control dispersement. The converse is also true. Hence, those having ordinary skill in the art will recognize that the categorization of a particular factor and/or sensor will depend upon the context of use of the factor and/or sensor. That is, if one designates that "something" be held constant or variable in an environment, one typically loses the ability to disseminate on the basis of that "something," and vice versa.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will appreciate that there are various vehicles by which processes and/or systems described herein can be effected (e.g., hardware, software, and/or firmware), and that the preferred vehicle will vary with the context in which the processes are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and/or processes via the use of block diagrams, flowcharts, and examples. Insofar as such block diagrams, flowcharts, and examples contain one or more functions and/or operations, it will be understood as notorious by those within the art that each function and/or operation within such block diagrams, flowcharts, or examples can be implemented, individually and/or collectively, by a wide range of hardware, software, firmware, or any combination thereof. In one embodiment, the present invention may be implemented via Application Specific Integrated Circuits (ASICs). However, those skilled in the art will recognize that the embodiments disclosed herein, in whole or in part, can be equivalently implemented in standard Integrated Circuits, as one or more computer programs running on one or more computers (e.g., as one or more server programs running on one or more computer systems), as one or more programs running on one or more processors (e.g., as one or more thin client programs running on one or more processors), as firmware, or as virtually any combination thereof, and that designing the circuitry and/or writing the code for the software or firmware would be well within the skill of one of ordinary skill in the art in light of this disclosure. In addition, those skilled in the art will appreciate that the mechanisms of the present invention are capable of being distributed as a program product in a variety of forms, and that an illustrative embodiment of the present invention applies equally regardless of the particular type of signal bearing media used to actually carry out the distribution. Examples of a signal bearing media include, but are not limited to, the following: recordable type media such as floppy disks, hard disk drives, CD ROMs, digital tape, and transmission type media such as digital and analogue communication links using TDM or IP based communication links (e.g., packet links).

In a general sense, those skilled in the art will recognize that the various embodiments described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configurable by a computer program (e.g., a general purpose computer configurable by a computer program or a microprocessor configurable by a computer program), electrical circuitry forming a memory device (e.g., any and all forms of random access memory), and electrical circuitry forming a communications device (e.g., a modem, communications switch, or optical-electrical equipment).

Those skilled in the art will recognize that it is common within the art to describe devices and/or processes in the fashion set forth herein, and thereafter use standard engineering practices to integrate such described devices and/or processes into data processing systems. That is, the devices and/or processes described herein can be integrated into a data processing system via a reasonable amount of experimentation. FIG. 1 shows an example representation of a data processing system into which at least a part of the herein described devices and/or processes may be integrated with a reasonable amount of experimentation.

With reference now again to FIG. 1, depicted is a pictorial representation of a conventional data processing system in which portions of the illustrative embodiments of the devices and/or processes described herein may be implemented. It should be noted that a graphical user interface systems (e.g., Microsoft Windows 98 or Microsoft Windows NT operating systems) and methods can be utilized with the data processing system depicted in FIG. 1. Data processing system 130 is depicted which includes system unit housing 132, video display device 134, keyboard 136, mouse 138, and microphone (not shown). Data processing system 130 may be implemented utilizing any suitable computer such as a DELL portable computer system, a product of Dell Computer Corporation, located in Round Rock, Tex.; Dell is a trademark of Dell Computer Corporation.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim element is intended, such an intent will be explicitly recited in the claim, and in the absence of such recitation no such intent is present. For example, as an aid to understanding, the following appended claims may contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to inventions containing only one such element, even when the same claim includes the introductory phrases "one or more" or "at least one" and indefinite articles such as "a" or "an"; the same holds true for the use of definite articles used to introduce claim elements. In addition, even if a specific number of an introduced claim element is explicitly recited, those skilled in the art will recognize that such recitation should typically be interpreted to mean at least the recited number (e.g., the bare recitation of "two elements," without other modifiers, typically means at least two elements, or two or more elements).

What is claimed is:

1. A method comprising:
   automatically controlling an environment of an inhalant chamber including maintaining an environmental factor via feedback control, wherein the environmental factor is a temperature of the inhalant chamber; and
   automatically controlling a concentration of an inhalant in the inhalant chamber.

2. The method of claim 1, wherein said maintaining an environmental factor via feedback control comprises:
   controlling the environmental factor via monitoring a temperature sensor.

3. The method of claim 2, wherein said controlling the environmental factor via monitoring a temperature sensor comprises:
   controlling the environmental factor via a Proportional Integral Derivative (PID) controller receiving input from the temperature sensor and adjusting a temperature driver.

4. A method comprising:
   automatically controlling a concentration of an inhalant in an inhalant chamber; and automatically controlling an environment of the inhalant chamber comprising:
maintaining an environmental factor via feedback control, wherein the environmental factor includes a humidity of the inhalant chamber.

5. The method of claim 4, wherein said maintaining an environmental factor via feedback control comprises:
controlling the environmental factor via monitoring a humidity sensor.

6. The method of claim 5, wherein said controlling the environmental factor via monitoring a humidity sensor comprises:
controlling the environmental factor via a Proportional Integral Derivative (PID) controller receiving input from the humidity sensor and adjusting a humidity driver.

7. A method comprising:
automatically controlling a concentration of an inhalant in an inhalant chamber; and
automatically controlling an environment of the inhalant chamber comprising:
maintaining an environmental factor via feedback control, wherein the environmental factor includes an airflow in to the inhalant chamber.

8. The method of claim 7, wherein said maintaining an environmental factor via feedback control comprises:
controlling the environmental factor via monitoring an input airflow sensor.

9. The method of claim 8, wherein said controlling the environmental factor via monitoring an input airflow sensor comprises:
controlling the environmental factor via a Proportional Integral Derivative (PID) controller receiving input from the input airflow sensor and adjusting an input airflow driver.

10. The method of claim 7, wherein said automatically controlling an environment of an inhalant chamber further comprises:
maintaining a second environmental factor via feedback control, wherein the second environmental factor includes a pressure of the inhalant chamber.

11. The method of claim 10, wherein said maintaining the second environmental factor via feedback control comprises:
controlling the second environmental factor via monitoring a pressure sensor of the inhalant chamber.

12. The method of claim 11, wherein said controlling the second environmental factor via monitoring the pressure sensor of the inhalant chamber comprises:
controlling the second environmental factor via a Proportional Integral Derivative (PID) controller receiving input from the pressure sensor and adjusting a pressure driver.

13. The method of claim 7, wherein said automatically controlling a concentration of an inhalant in the inhalant chamber further comprises:
dispersing either an organic or inorganic substance via electronic control of one.

14. The method of claim 13, wherein said dispersing either an organic or inorganic substance via electronic control of one or more inhalant dissemination devices comprises:
dispersing a substance having a wet aerosol form.

15. The method of claim 13, wherein said dispersing either an organic or inorganic substance via electronic control of one or more inhalant dissemination devices comprises:
dispersing a substance having a aerosol form.

16. The method of claim 13, wherein said dispersing either an organic or inorganic substance via electronic control of one or more inhalant dissemination devices comprises:
dispersing a substance having a gaseous substance form.

17. The method of claim 13, wherein said dispersing either an organic or inorganic substance via electronic control of one or more inhalant dissemination devices comprises:
dispersing a substance having a mist form.

18. The method of claim 13, wherein said dispersing either an organic or inorganic substance via electronic control of one or more inhalant dissemination devices comprises:
dispersing a substance having a fog form.

19. The method of claim 13, wherein said dispersing either an organic or inorganic substance via electronic control of one or more inhalant dissemination devices comprises:
dispersing a substance having a fume form.

20. The method of claim 13, wherein said dispersing either an organic or inorganic substance via electronic control of one or more inhalant dissemination devices comprises:
dispersing a substance having an airborne substance form.

21. The method of claim 13, wherein said dispersing either an organic or inorganic substance via electronic control of one or more inhalant dissemination devices comprises:
controlling the one or more inhalant dissemination devices via a Proportional Integral Derivative (PID) controller receiving input from a chamber pressure monitor.

22. The method of claim 13, wherein said dispersing either an organic or inorganic substance via electronic control of one or more inhalant dissemination devices comprises:
controlling the one or more inhalant dissemination devices via a Proportional Integral Derivative (PID) controller receiving input from an inhalant-concentration sensor.

23. The method of claim 13, wherein said dispersing either an organic or inorganic substance via electronic control of one or more inhalant dissemination devices comprises:
controlling the one or more inhalant dissemination devices via a Proportional Integral Derivative (PID) controller receiving input from a gas sensor.

24. The method of claim 7, further comprising:
displaying near real time measurement data related to an animal in the inhalant chamber.

25. The method of claim 7 wherein at least a portion of an animal extends into the chamber.

26. The method of claim 7 wherein gaseous input and gaseous egress from the inhalant chamber are controlled.

27. A method comprising:
automatically controlling a concentration of an inhalant in an inhalant chamber; and
automatically controlling an environment of the inhalant chamber comprising:
maintaining an environmental factor via feedback control, wherein the environmental factor includes an exhaust airflow out of the inhalant chamber.

28. The method of claim 27, wherein said maintaining an environmental factor via feedback control comprises:
controlling the environmental factor via monitoring an exhaust output airflow sensor.

29. The method of claim 28, wherein said controlling the environmental factor via monitoring an exhaust output airflow sensor comprises:
controlling the environmental factor via a Proportional Integral Derivative (PID) controller receiving input from the output airflow sensor and adjusting an exhaust output airflow driver.

30. A method comprising:
automatically controlling an environment of an inhalant chamber; and
automatically controlling a concentration of an inhalant in the inhalant chamber comprising:
controlling a flow rate out of the inhalant chamber in response to a specified dispensement of the inhalant.

31. The method of claim 30, wherein said controlling a flow rate out of the inhalant chamber in response to a specified dispensement of the inhalant comprises:
controlling the flow rate out of the inhalant chamber via a Proportional Integral Derivative (PID) controller receiving input from an inhalant concentration sensor.

32. The method of claim 30, wherein said controlling a flow rate out of the inhalant chamber in response to a specified dispensement of the inhalant comprises:
controlling the flow rate out of the inhalant chamber via a Proportional Integral Derivative (PID) controller receiving input from a gas sensor.

33. The method of claim 30, wherein said controlling a flow rate out of the inhalant chamber in response to a specified dispensement of the inhalant comprises:
controlling the flow rate out of the inhalant chamber via a Proportional Integral Derivitive (PID) controller receiving input from an input airflow sensor.

34. The method of claim 30, wherein said controlling a flow rate out of the inhalant chamber in response to a specified dispensement of the inhalant comprises:
controlling the flow rate out of the inhalant chamber via a Proportional Integral Derivative (PID) controller receiving input from an output airflow sensor.

35. A method comprising:
automatically controlling an environment of an inhalant chamber;
automatically controlling a concentration of an inhalant in the inhalant chamber; and
displaying near real time measurement data related to an animal in an inhalant chamber comprising:
displaying animal-related dosimetry data.

36. The method of claim 35, wherein said displaying near real time measurement data related to an animal in an inhalant chamber further comprises:
displaying a temperature of the inhalant chamber.

37. The method of claim 35, wherein said displaying near real time measurement data related to an animal in an inhalant chamber further comprises:
displaying a humidity of the inhalant chamber.

38. The method of claim 35, wherein said displaying near real time measurement data related to an animal in an inhalant chamber further comprises:
displaying an airflow into the inhalant chamber.

39. The method of claim 35, wherein said displaying near real time measurement data related to an animal in an inhalant chamber further comprises:
displaying an airflow out of the inhalant chamber.

40. The method of claim 35, wherein said displaying near real time measurement data related to an animal in an inhalant chamber further comprises:
displaying animal-related respiration data.

41. The method of claim 35, wherein said displaying near real time measurement data related to an animal in an inhalant chamber further comprises:
displaying a pressure of the inhalant chamber.

42. A system comprising:
means for automatically controlling a concentration of an inhalant in an inhalant chamber; and
means for automatically controlling an environment of the inhalant chamber comprising:
means for maintaining an environmental factor via feedback control, wherein the environmental factor includes an airflow in to the inhalant chamber.

43. The system of claim 42, wherein said means for maintaining an environmental factor via feedback control comprises:
means for controlling the environmental factor via monitoring an input airflow sensor.

44. The system of claim 43, wherein said means for controlling the environmental factor via monitoring an input airflow sensor comprises:
means for controlling the environmental factor via a Proportional Integral Derivative (PID) controller receiving input from the input airflow sensor and adjusting an input airflow driver.

45. The system of claim 42, wherein said means for automatically controlling an environment of an inhalant chamber further comprises:
maintaining a second environmental factor via feedback control, wherein the second environmental factor includes a pressure of the inhalant chamber.

46. The system of claim 45, wherein said means for maintaining a second environmental factor via feedback control comprises:
means for controlling the second environmental factor via monitoring a pressure sensor of the inhalant chamber.

47. The system of claim 46, wherein said means for controlling the second environmental factor comprises:
means for controlling the environmental factor via a Proportional Integral Derivative (PID) controller receiving input from the pressure sensor and adjusting a pressure driver.

48. The system of claim 42, wherein said means for automatically controlling a concentration of an inhalant in the inhalant chamber comprises:
means for dispersing either an organic or inorganic substance via electronic control of one or more inhalant dissemination devices.

49. The system of claim 42 further comprising:
means for displaying near real time measurement data related to an animal in the inhalant chamber.

50. The system of claim 49, wherein said means for displaying near real time measurement data related to an animal in an inhalant chamber comprises:
means for displaying a pressure of the inhalant chamber.

51. The system of claim 42, wherein said means for automatically controlling an environment of an inhalant chamber further comprises:
means for maintaining a second environmental factor via feedback control, wherein the second environmental factor is a temperature of the inhalant chamber.

52. The system of claim 51, wherein said means for maintaining the second environmental factor via feedback control comprises:

means for controlling the second environmental factor via monitoring a temperature sensor.

53. The system of claim 52, wherein said means for controlling the second environmental factor via monitoring the temperature sensor comprises:

means for controlling the second environmental factor via a Proportional Integral Derivative (PID) controller receiving input from the temperature sensor and adjusting a temperature driver.

54. The system of claim 42, wherein said means for automatically controlling an environment of an inhalant chamber further comprises:

means for maintaining a second environmental factor via feedback control, wherein the second environmental factor includes a humidity of the inhalant chamber.

55. The system of claim 54, wherein said means for maintaining the second environmental factor via feedback control comprises:

means for controlling the second environmental factor via monitoring a humidity sensor.

56. The system of claim 55, wherein said means for controlling the second environmental factor via monitoring a humidity sensor comprises:

means for controlling the second environmental factor via a Proportional Integral Derivative (PID) controller receiving input from the humidity sensor and adjusting a humidity driver.

57. The system of claim 42 wherein at least a portion of an animal extends into the chamber.

58. The system of claim 42 wherein gaseous input and gaseous egress from the inhalant chamber are controlled.

59. A system comprising:

means for automatically controlling a concentration of an inhalant in an inhalant chamber; and means for automatically controlling an environment of the inhalant chamber comprising:

means for maintaining an environmental factor via feedback control, wherein the environmental factor includes an exhaust airflow out of the inhalant chamber.

60. The system of claim 59, wherein said means for maintaining the environmental factor via feedback control comprises:

means for controlling the environmental factor via monitoring an exhaust output airflow sensor.

61. The system of claim 60, wherein said means for controlling the environmental factor via monitoring an exhaust output airflow sensor comprises:

means for controlling the environmental factor via a Proportional Integral Derivative (PID) controller receiving input from the output airflow sensor and adjusting an exhaust output airflow driver.

62. A The system comprising:

means for automatically controlling an environment of an inhalant chamber; and means for automatically controlling a concentration of an inhalant in the inhalant chamber comprising means for dispersing either an organic or inorganic substance via electronic control of one or more inhalant dissemination devices, said means for dispersing either an organic or inorganic substance comprising:

means for dispersing a substance having a wet aerosol form.

63. The system of claim 62, wherein said means for dispersing either an organic or inorganic substance via electronic control of one or more inhalant dissemination devices further comprises:

means for dispersing a substance having a dry aerosol form.

64. The system of claim 62, wherein said means for dispersing either an organic or inorganic substance via electronic control of one or more inhalant dissemination devices further comprises:

means for dispersing a substance having a gaseous substance form.

65. The system of claim 62, wherein said means for dispersing either an organic or inorganic substance via electronic control of one or more inhalant dissemination devices further comprises:

means for dispersing a substance having a mist form.

66. The system of claim 62, wherein said means for dispersing either an organic or inorganic substance via electronic control of one or more inhalant dissemination devices further comprises:

means for dispersing a substance having a fog form.

67. The system of claim 62, wherein said means for dispersing either an organic or inorganic substance via electronic control of one or more inhalant dissemination devices further comprises:

means for dispersing a substance having a fume form.

68. The system of claim 62, wherein said means for dispersing either an organic or inorganic substance via electronic control of one or more inhalant dissemination devices further comprises:

means for dispersing a substance having an airborne substance form.

69. The system of claim 62, wherein said means for dispersing either an organic or inorganic substance via electronic control of one or more inhalant dissemination devices comprises:

means for controlling the one or more inhalant dissemination devices via a Proportional Integral Derivative (PID) controller receiving input from a chamber pressure monitor.

70. The system of claim 62, wherein said means for dispersing either an organic or inorganic substance via electronic control of one or more inhalant dissemination devices comprises:

means for controlling the one or more inhalant dissemination devices via a Proportional Integral Derivative (PID) controller receiving input from an inhalant-concentration sensor.

71. The system of claim 62, wherein said means for dispersing either an organic or inorganic substance via electronic control of one or more inhalant dissemination devices comprises:

means for controlling the one or more inhalant dissemination devices via a Proportional Integral Derivative (PID) controller receiving input from a gas sensor.

72. A system comprising:

means for automatically controlling an environment of an inhalant chamber; and means for automatically controlling a concentration of an inhalant in the inhalant chamber comprising:

means for controlling a flow rate out of the inhalant chamber in response to a specified dispensement of the inhalant.

73. The system of claim 72, wherein said means for controlling a flow rate out of the inhalant chamber in response to a specified dispensement of the inhalant comprises:

means for controlling the flow rate out of the inhalant chamber via a Proportional Integral Derivative (PID) controller receiving input from an inhalant concentration sensor.

74. The system of claim 72, wherein said means for controlling a flow rate out of the inhalant chamber in response to a specified dispensement of the inhalant comprises:

means for controlling the flow rate out of the inhalant chamber via a Proportional Integral Derivative (PID) controller receiving input from a gas sensor.

75. The system of claim 72, wherein said means for controlling a flow rate out of the inhalant chamber in response to a specified dispensement of the inhalant comprises:

means for controlling the flow rate out of the inhalant chamber via a Proportional Integral Derivative (PID) controller receiving input from an input airflow sensor.

76. The system of claim 72, wherein said means for controlling a flow rate out of the inhalant chamber in response to a specified dispensement of the inhalant comprises:

means for controlling the flow rate out of the inhalant chamber via a Proportional Integral Derivative (PID) controller receiving input from an output airflow sensor.

77. A system comprising:

means for automatically controlling an environment of an inhalant chamber;

means for automatically controlling a concentration of an inhalant in the inhalant chamber;

means for displaying near real time measurement data related to an animal in the inhalant chamber comprising:

means for displaying animal-related dosimetry data.

78. The system of claim 77, wherein said means for displaying near real time measurement data related to an animal in the inhalant chamber further comprises:

means for displaying a temperature of the inhalant chamber.

79. The system of claim 77, wherein said means for displaying near real time measurement data related to an animal in the inhalant chamber comprises:

means for displaying a humidity of the inhalant chamber.

80. The system of claim 77, wherein said means for displaying near real time measurement data related to an animal in the inhalant chamber further comprises:

means for displaying an airflow into the inhalant chamber.

81. The system of claim 77, wherein said means for displaying near real time measurement data related to an animal in the inhalant chamber comprises:

means for displaying an airflow out of the inhalant chamber.

* * * * *